US007531507B2

(12) United States Patent
Von Nussbaum et al.

(10) Patent No.: US 7,531,507 B2
(45) Date of Patent: May 12, 2009

(54) ACYLATED NONADEPSIPEPTIDES CONTAINING PYRIDYL ALANINE RESIDUES

(75) Inventors: Franz Von Nussbaum, Duesseldorf (DE); Nina Brunner, Essen (DE); Rainer Endermann, Wuppertal (DE); Chantal Fuerstner, Muelheim/Ruhr (DE); Elke Hartmann, Wuppertal (DE); Holger Paulsen, Hilden (DE); Jacques Ragot, Duesseldorf (DE); Guido Schiffer, Wuppertal (DE); Joachim Schuhmacher, Wuppertal (DE); Niels Svenstrup, Velbert (DE); Joachim Telser, Wuppertal (DE); Sonja Anlauf, Wuppertal (DE); Michael-Alexander Bruening, Berlin (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 11/267,063

(22) Filed: Nov. 4, 2005

(65) Prior Publication Data

US 2006/0264358 A1 Nov. 23, 2006

(30) Foreign Application Priority Data

Nov. 5, 2004 (DE) .................. 10 2004 053 407

(51) Int. Cl.
*A61K 38/00* (2006.01)
*A61K 38/12* (2006.01)
*A61K 39/00* (2006.01)
*C07K 7/00* (2006.01)
*C07K 7/54* (2006.01)
*C07K 9/00* (2006.01)

(52) U.S. Cl. .................. 514/9; 514/2; 514/11; 514/15; 530/300; 530/317; 530/328

(58) Field of Classification Search ..................... 514/9; 530/317, 328
See application file for complete search history.

(56) References Cited

U.S. PATENT DOCUMENTS

| 4,754,018 A | 6/1988 | Tymiak et al. |
| 2005/0075281 A1* | 4/2005 | Von Nussbaum et al. ...... 514/9 |

FOREIGN PATENT DOCUMENTS

| EP | 0 196 042 | 10/1986 |
| JP | 01132600 | 5/1989 |
| WO | WO-2004/099239 | 11/2004 |

OTHER PUBLICATIONS

Bacterial Urinary Tract Infections from the Merck manual.*
Cellulitis from the Merck manual.*
Cystic Fibrosis from the Merck manual.*
Baquero, J. Antimicrob. Chemother. (1997) 39(Suppl. A):1-6.
Bonner et al., J. Antibiot. (1988) 41:1745-1751.
Goldrick, Am. J. Nurs. (2002) 102:17.
Green, Expert Opin. Ther. Targets (2002) 6:1-19.
Johnson et al., J. Hosp. Infect. (2001) 49(Suppl. A):3-11.
Kato et al., J. Antibiot. (1988) 41:719-725.
Merget et al., Organomet. Chem. (2001) 628:183-194.
Neises et al., Org. Synth. (1985) 63:183-187.
O'Sullivan et al., J. Antibiot. (1988) 41:1740-1744.
Schuhmacher et al., Journal of Pharmaceutical Sciences (2004) 93:816-830.
Shoji et al., J. Antibiot. (1988) 41:713-718.
Tymiak et al., J. Org. Chem. (1989) 54:1149-1157.
Biochemical Journal (1984) 219:345-373.

* cited by examiner

*Primary Examiner*—Anish Gupta
*Assistant Examiner*—Julie Ha
(74) *Attorney, Agent, or Firm*—Morrison & Foerster LLP

(57) ABSTRACT

The invention relates to nonadepsipeptides and processes for their preparation, and to their use for producing medicaments for the treatment and/or prophylaxis of diseases, in particular bacterial infectious diseases.

9 Claims, No Drawings

ACYLATED NONADEPSIPEPTIDES CONTAINING PYRIDYL ALANINE RESIDUES

The invention relates to nonadepsipeptides and processes for their preparation, and to their use for producing medicaments for the treatment and/or prophylaxis of diseases, in particular bacterial infectious diseases.

The bacterial cell wall is synthesized by a number of enzymes (cell wall biosynthesis) and is essential for the survival and reproduction of microorganisms. The struture of this macromolecule, as well as the proteins involved in the synthesis thereof, are highly conserved within the bacteria. Owing to its essential nature and uniformity, cell wall biosynthesis is an ideal point of attack for novel antibiotics (D. W. Green, The bacterial cell wall as a source of antibacterial targets, *Expert Opin. Ther. Targets*, 2002, 6, 1-19).

Vancomycin and penicillins are inhibitors of bacterial cell wall biosynthesis and are successful examples of the antibiotic potency of this principle of action. They have been employed for several decades clinically for the treatment of bacterial infections, especially with Gram-positive pathogens. The growing occurrence of resistant microbes, e.g. methicillin-resistant staphylococci, penicillin-resistant pneumococci and vancomycin-resistant enterococci (F. Baquero, Gram-positive resistance: challenge for the development of new antibiotics, *J. Antimicrob. Chemother.*, 1997, 39, Suppl A: 1-6; A. P. Johnson, D. M. Livermore, G. S. Tillotson, Antimicrobial susceptibility of Gram-positive bacteria: what's current, what's anticipated?, *J. Hosp. Infect.*, 2001, (49), Suppl A: 3-11) and recently also for the first time vancomycin-resistant staphylococci (B. Goldrick, First reported case of VRSA in the United States, *Am. J. Nurs.*, 2002, 102, 17) means that these substances are increasingly losing their therapeutic efficacy.

The present invention describes a novel class of cell wall biosynthesis inhibitors without cross resistance with known antibiotic classes.

The natural product lysobactin and some derivatives are described as having antibacterial activity in U.S. Pat. No. 4,754,018. The isolation and antibacterial activity of lysobactin is also described in EP-A-196 042 and JP 01132600. WO04/099239 describes derivatives of lysobactin having antibacterial activity.

The antibacterial effect of lysobactin and katanosin A is furthermore described in O'Sullivan, J. et al., *J. Antibiot.* 1988, 41, 1740-1744, Bonner, D. P. et al., *J. Antibiot.* 1988, 41, 1745-1751, Shoji, J. et al., *J. Antibiot.* 1988, 41, 713-718 and Tymiak, A. A. et al., *J. Org. Chem.* 1989, 54, 1149-1157.

One object of the present invention is to provide alternative compounds with comparable or improved antibacterial effect and better tolerability, e.g. less nephrotoxicity, and better distribution in the body, i.e. better pharmacokinetic properties such as, for example, increase in the free fraction ($f_u$), for the treatment of bacterial diseases in humans and animals.

The invention relates to compounds of the formula

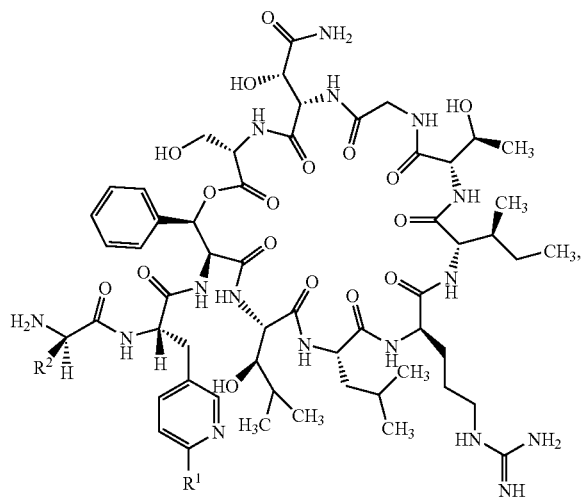

(I)

in which $R^1$ is hydrogen, and $R^2$ is 2,2-dimethylbut-1-yl, 2-ethyl-2-methylbut-1-yl, 2,2-diethylbut-1-yl, 2,2-dimethylpent-1-yl or trimethylsilylmethyl, or $R^1$ is trifluoromethyl, and $R^2$ is 2,2-dimethylprop-1-yl, 2,2-dimethylbut-1-yl, 2-ethyl-2-methylbut-1-yl, 2,2-diethylbut-1-yl, 2,2-dimethylpent-1-yl or trimethylsilylmethyl, and their salts, their solvates and the solvates of their salts.

Compounds of the invention are compounds of the formula (I) and the salts, solvates, solvates of the salts and prodrugs thereof, the compounds which are encompassed by formula (I) and are of the formulae mentioned below, and the salts, solvates, solvates of the salts and prodrugs thereof, and the compounds which are encompassed by formula (I) and are mentioned below as exemplary embodiments, and the salts, solvates, solvates of the salts and prodrugs thereof, where the compounds which are encompassed by formula (I) and are mentioned below are not already salts, solvates, solvates of the salts and prodrugs.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated from such mixtures of enantiomers and/or diastereomers in a known manner.

Where the compounds of the invention can exist in tautomeric forms, the present invention encompasses all tautomeric forms.

Salts preferred for the purposes of the present invention are physiologically acceptable salts of the compounds of the invention. However, also included are salts which are not themselves suitable for pharmaceutical applications but can be used for example for the isolation or purification of the compounds of the invention, or mixed salts. A mixed salt means for the purposes of the present invention an addition salt which comprises two or more different acids or bases, such as, for example, a trifluoroacetate-mesylate salt.

Physiologically acceptable salts of the compounds of the invention include acid addition salts of mineral acids, car boxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds of the invention which form a complex in the solid or liquid state through coordination with solvent molecules. Hydrates are a special form of solvates in which the coordination takes place with water.

Preference is given to compounds of the formula (I), in which
$R^1$ is hydrogen, and
$R^2$ is 2,2-dimethylbut-1-yl or trimethylsilylmethyl,
or
$R^1$ is trifluoromethyl, and
$R^2$ is 2,2-dimethylprop-1-yl, 2,2-dimethylbut-1-yl or trimethylsilylmethyl,
and their salts, their solvates and the solvates of their salts.

Preference is also given to compounds of the formula (I) in which
$R^1$ is hydrogen, and
$R^2$ is 2,2-dimethylbut-1-yl, 2-ethyl-2-methylbut-1-yl, 2,2-diethylbut-1-yl or trimethylsilylmethyl,
and their salts, their solvates and the solvates of their salts.

Preference is also given to compounds of the formula (I) in which
$R^1$ is hydrogen, and
$R^2$ is 2,2-dimethylbut-1-yl, 2-ethyl-2-methylbut-1-yl, 2,2-diethylbut-1-yl, 2,2-dimethylpent-1-yl or trimethylsilylmethyl.

Particular preference is given to the compound 3-(trimethylsilyl)-D-alanyl-3-(pyridin-3-yl)-L-alanyl-de(1-D-leucyl-2-L-leucyl)-lysobactin

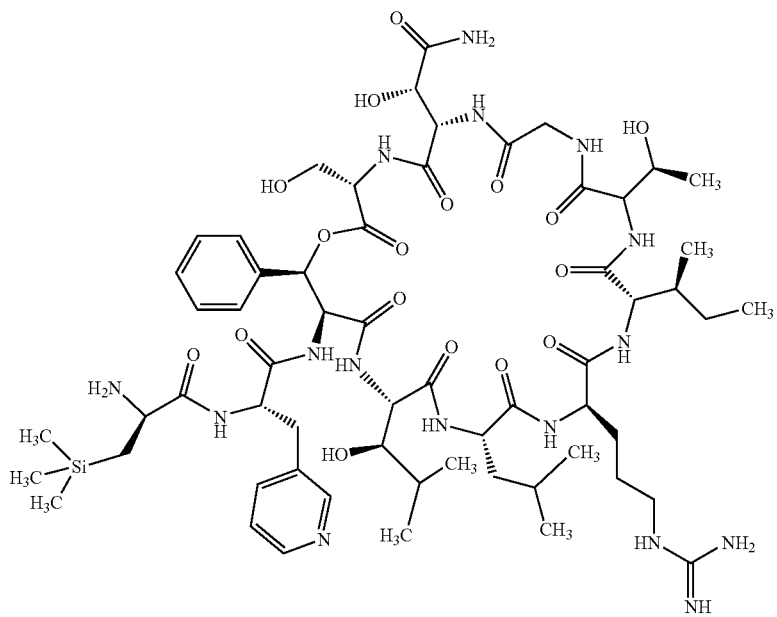

or one of its salts, its solvates or the solvates of its salts.

The invention further relates to a process for preparing the compounds of the formulae (I), where the compound of the formula

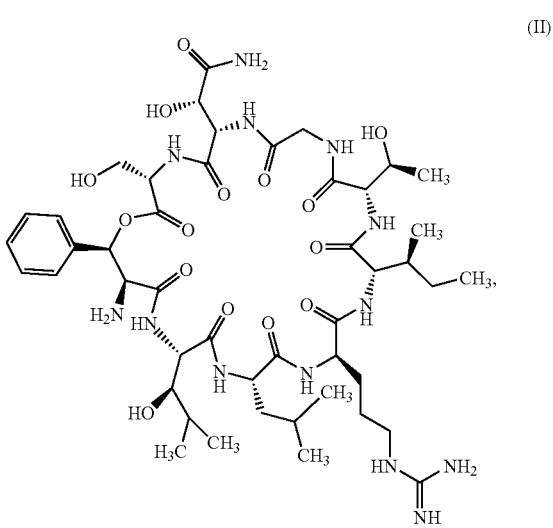

(II)

are reacted with compounds of the formula

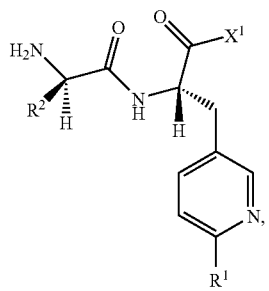

(III)

in which

R¹ and R² have the meaning indicated above, and $X^1$ is halogen, preferably bromine, chlorine or fluorine, or hydroxy.

If $X^1$ is halogen, the reaction generally takes place in inert solvent, where appropriate in the presence of a base, preferably in a temperature range from −30° C. to 50° C. under atmospheric pressure.

Examples of inert solvents are tetrahydrofuran, methylene chloride, pyridine, dioxane or dimethylformamide, with preference for methylene chloride or dimethylformamide.

Examples of bases are triethylamine, diisopropylethylamine or N-methylmorpholine, with preference for diisopropylethylamine.

If $X^1$ is hydroxy, the reaction generally takes place in inert solvents in the presence of a dehydrating reagent, where appopriate in the presence of a base, preferably in a temperature range from −30° C. to 50° C. under atmospheric pressure.

Examples of inert solvents are halohydrocarbons such as dichloromethane or trichloromethane, hydrocarbon such as benzene, nitromethane, dioxane, dimethylformamide or acetonitrile. It is likewise possible to employ mixtures of these solvents. Dichloromethane or dimethylformamide is particularly preferred.

Examples of dehydrating reagents suitable in this connection are carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-2-oxo-1-(2H)-pyridyl)-1,1,3,3-tetramethyluronium tetrafluoroborate (TPTU) or O-(7-azabenzotriazol-1-yl-N,N,N',N'-tetramethyluronium hexafluorophosphate (HATU), or 1-hydroxybenzotriazole (HOBt), or benzotriazol-1-yloxytris(dimethylamino) phosphonium hexafluorophosphate (BOP), or N-hydroxysuccinimide, or mixtures thereof, with bases.

Examples of bases are alkali metal carbonates, such as, for example, sodium or potassium carbonate, or bicarbonate, or organic bases such as trialkylamines, e.g. triethylamine, N-methylmorpholine, N-methylpiperidine, 4-dimethylaminopyridine or diisopropylethylamine.

The condensation is preferably carried out with HATU or with EDC in the presence of HOBt.

The compounds of the formula (III) carry protective groups where appropriate, so that in these cases the reaction of the compound of the formula (II) with compounds of the formula (III) is followed by elimination of the protective groups with trifluoroacetic acid by methods known to the skilled persion.

The free base of the salts of the compounds of the formula (I) can be obtained for example by adding a base and subsequently extracting or precipitating the compound or separating it by chromatography by processes known to the skilled person, in particular by use of polymer-bound bases such as, for example, polymer-bound bicarbonate.

The invention further relates to a process for preparing the compounds of the formula (I) or their salts according to Claim 1, in which salts of the compounds or solvates of the salts of the compounds are converted into the compounds by adding a base.

The compound of the formula (II) can be synthesized by double Edmann degradation from lysobactin (Example 1A), as described in Example 2A in the experimental section.

The compounds of the formula (III) are known or can be synthesized by known processes from the appropriate precursors.

The preparation of the compounds of the invention can be illustrated by the following synthesis scheme.

Synthesis scheme:
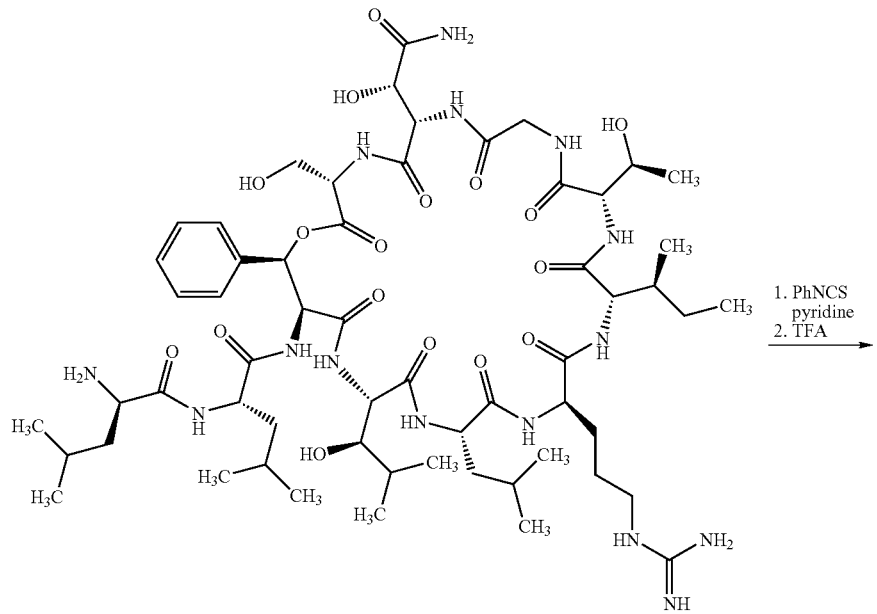
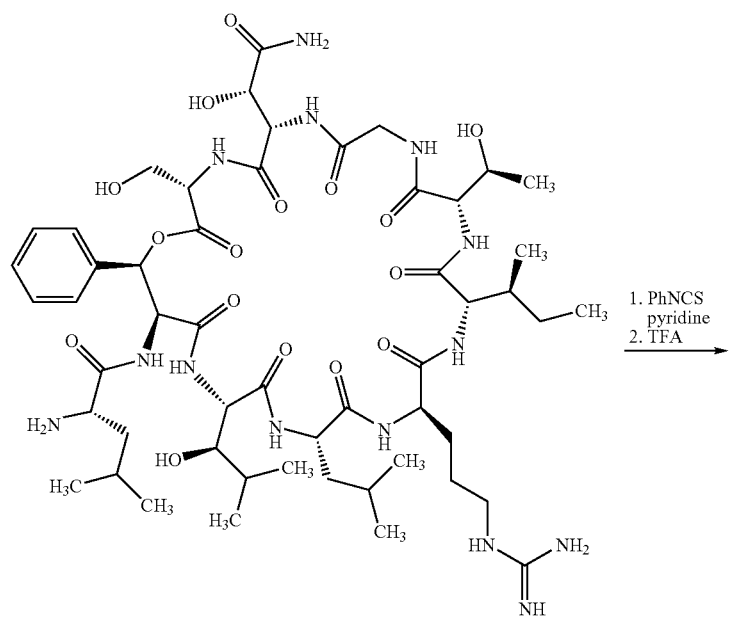

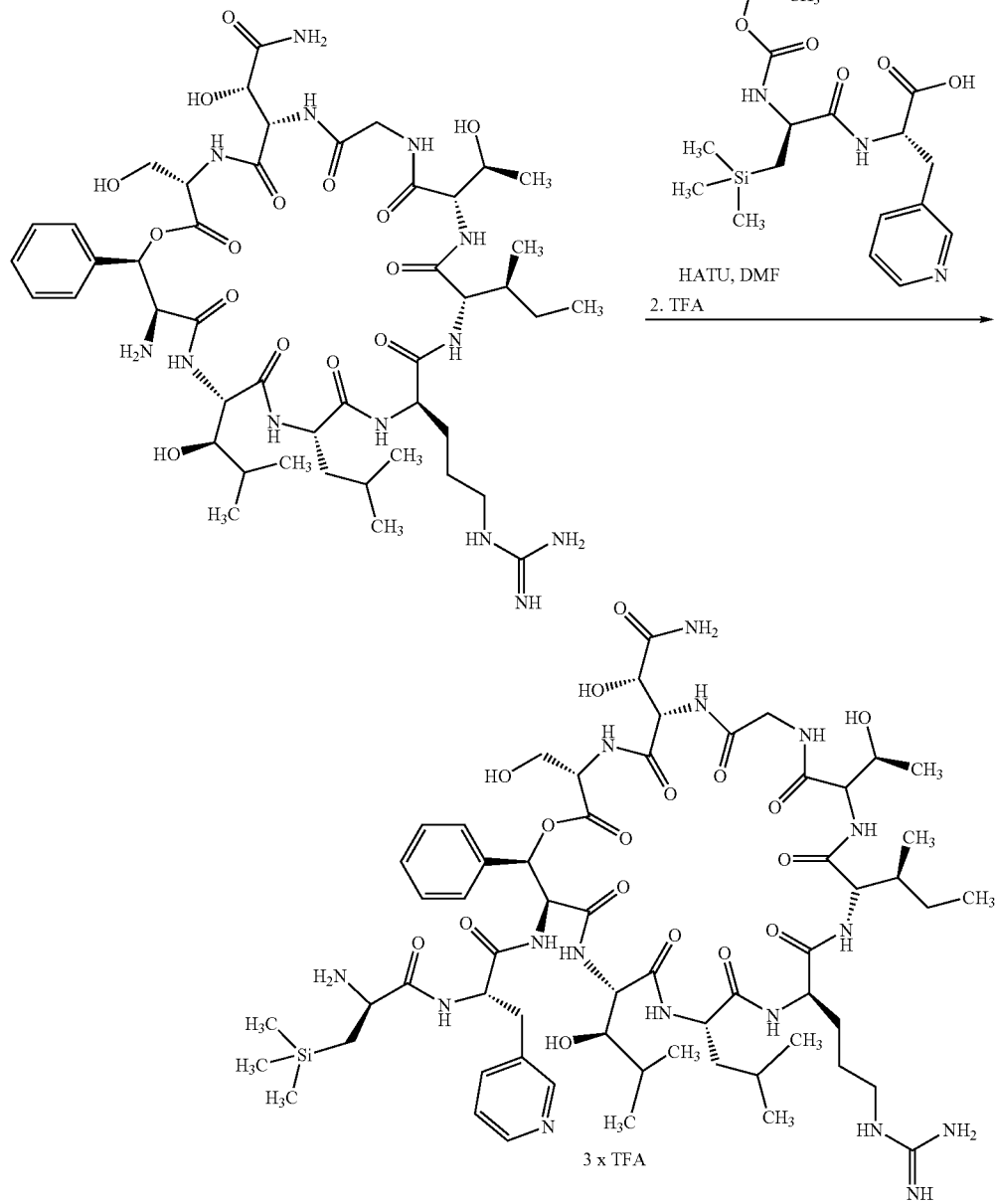

The compounds of the invention show a valuable range of pharmacological and pharamacokinetic effects which could not have been predicted. They shown an antibacterial effect.

They are therefore suitable for use as medicaments for the treatment and/or prophylaxis of diseases in humans and animals.

The compounds of the invention are distinguished by low nephrotoxicity compared with lysobactin aus.

The compounds of the invention are distinguished by better pharmacokinetics compared with lysobactin. While the pharmacological effect is the same or improved, they show a better distribution in the body, resulting in a lower therapeutic dose and a wider therapeutic treatment window.

The compounds of the invention have a higher free fraction ($f_u$) in plasma than lysobactin.

The described nonadepsipeptides act as inhibitors of bacterial cell wall biosynthesis.

The preparations of the invention are particularly effective for bacteria and bacteroid microorganisms. They are therefore particularly suitable for the prophylaxis and chemotherapy of local and systemic infections caused by these pathogens in human and veterinary medicine.

The preparations of the invention can in principle be used against all bacteria and bacteroid microorganisms possessing a bacterial cell wall (murein sacculus) and the relevant enzyme systems, for example the following pathogens or mixtures of the following pathogens:

Gram-negative cocci (*Neisseria gonorrhoeae*) and Gram-negative rods such as enterobacteriaceae, e.g. *Escherichia coli, Haemophilus influenzae, Pseudomonas, Klebsiella, Citrobacter* (*C. freundii, C. divernis*), *Salmonella* and *Shigella*;

also *Enterobacter* (*E. aerogenes, E. agglomerans*), *Hafnia, Serratia* (*S. marcescens*), *Providencia, Yersinia*, and the genus *Acinetobacter, Branhamella* and *Chlamydia*. The antibacterial ranges additionally includes strictly anaerobic bacteria such as, for example, *Bacteroides fragilis*, representatives of the genus *Peptococcus, Peptostreptococcus*, and the genus *Clostridium*; in addition mycobacteria, e.g. *M. tuberculosus*. The compounds of the invention show a particularly pronounced effect on Gram-positive cocci, e.g. Staphylococci (*S. aureus, S. epidermidis, S. haemolyticus, S. carnosus*), enterococci (*E. faecalis, E. faecium*) and streptococci (*S. agalactiae, S. pneumoniae, S. pyogenes*).

The above list of pathogens is mainly by way of example and is by no means to be interpreted restrictively. Examples which may be mentioned of diseases which are caused by the pathogens mentioned or mixed infections and can be prevented, improved or healed by the preparations of the invention are:

Infectious diseases in humans such as, for example, uncomplicated and complicated urinary tract infections, uncomplicated cutaneous and superficial infections, complicated cutaneous and soft tissue infections, hospital- and community-acquired pneumonia, nosocomial pneumonias, acute exacerbations and secondary bacterial infections of chronic bronchitis, acute otitis media, acute sinusitis, streptococcal pharyngitis, bacterial meningitis, uncomplicated gonococcal and non-gonococcal urethritis/cervicitis, acute prostatitis, endocarditis, uncomplicated and complicated intra-abdominal infections, gynaecological infections, pelvic inflammatory disease, bacterial vaginosis, acute and chronic osteomyelitis, acute bacterial arthritis, empirical therapy in febrile neutropenic patients, also bacteraemias, MRSA infections, acute infectious diarrhoea, *Helicobacter pylori* infections, postoperative infections, odontogenic infections, ophthalmological infections, postoperative infections (including periproctal abscess, wound infections, biliary infections, mastitis and acute appendicitis), cystic fibrosis and bronchiectasis.

Apart from humans, bacterial infections can be treated in other species. Examples which may be mentioned are:

Pigs: diarrhoea, enterotoxaemia, sepsis, dysentery, salmonellosis, mastitis-metritis-agalactiae syndrome, mastitis;

Ruminants (cattle, sheep, goats): diarrhoea, sepsis, bronchopneumonia, salmonellosis, pasteurellosis, genital infections;

Horses: bronchopneumonia, joint ill, puerperal and post-puerperal infections, salmonellosis;

Dogs and cats: bronchopneumonia, diarrhoea, dermatitis, otitis, urinary tract infections, prostatitis;

Poulty (hens, turkeys, quail, pigeons, ornamental birds and others): *E. coli* infections, chronic airway disorders, salmonellosis, pasteurellosis, psittacosis.

It is likewise possible to treat bacterial diseases in the rearing and management of productive and ornamental fish, in which case the antibacterial spectrum is extended beyond the pathogens mentioned above to further pathogens such as, for example, *Pasteurella, Brucella, Campylobacter, Listeria, Erysipelothris, Corynebacteria, Borellia, Treponema, Nocardia, Rickettsia, Yersinia*.

The present invention further relates to the use of the compounds of the invention for the treatment and/or prophylaxis of diseases, in particular of bacterial infectious diseases.

The present invention further relates to the use of the compounds of the invention for the treatment and/or prophylaxis of diseases, especially of the aforementioned diseases.

The present invention further relates to the use of the compounds of the invention for producing a medicament for the treatment and/or prophylaxis of diseases, especially of the aforementioned diseases.

The compounds of the invention are preferably used to produce medicaments suitable for the prophylaxis and/or treatment of bacterial diseases.

The present invention further relates to a method for the treatment and/or prophylaxis of diseases, especially of the aforementioned diseases, by using an antibacterially effective amount of the compounds of the invention.

The present invention further relates to medicaments comprising at least one compound of the invention and at least one or more further active ingredients, in particular for the treatment and/or prophylaxis of the aforementioned diseases. Preferred active ingredients for combination are compounds having antibacterial activity and having a different range of effects, in particular a supplementary range of effects, and/or being synergistic to the compounds of the invention.

The compounds of the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. anti-oxidants such as, for example, ascorbic acid), colours (e.g. inorganic pigments such as, for example, iron oxides) and masking flavours and/or odours.

The present invention further relates to medicaments which comprise at least one compound of the invention, normally together with one or more inert, nontoxic, pharmaceutically suitable excipients, and to the use thereof for the aforementioned purposes.

It has generally proved advantageous to administer on intravenous administration amounts of about 0.001 to 100 mg/kg, preferably about 0.1 to 10 mg/kg, of bodyweight to achieve effective results, and on oral administration the dosage is about 0.01 to 50 mg/kg, preferably 0.5 to 10 mg/kg, of bodyweight.

It may nevertheless be necessary where appropriate to deviate from the stated amounts, in particular as a function of the bodyweight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The percentage data in the following tests and examples are, unless indicated otherwise, per centages by weight; parts are parts by weight. Solvent ratios, dilution ratios and concentration data for the liquid/liquid solutions are in each case based on volume.

A. EXAMPLES

Abbreviations
aq. aqueous
area (peak) area
BHI brain heart infusion
Boc tert-butyloxycarbonyl
br. broad signal (in NMR spectra)
calc. calculated
conc. concentrated
D doublet (in NMR spectra)
DCI direct chemical ionization (in MS)
DCM dichloromethane
DIEA N,N-diisopropylethylamine
DMAP N,N-diisopropylethylamine
DMSO dimethyl sulphoxide
DMF N,N-dimethylformamide
EA ethyl acetate (acetic acid ethyl ester)
EDC 1-ethyl-3-(3-dimethylaminopropyl)carbodiimide (also EDCI)
EDCxHCl 1-ethyl-3-(3-dimethylaminopropyl)carbodiimide hydrochloride
EI electron impact ionization (in MS)
ESI electrospray ionization (in MS)
ESIneg anion scan in ESI mass spectroscopy
ESIpos cation scan in ESI mass spectroscopy
Ex. example
h hour
HATU O-(7-azabenzotriazol-1-yl)-N,N,N',N'-tetramethyluronium hexafluorophosphate
HOBt 1-hydroxybenzotriazole
HPLC high pressure, high performance liquid chromatography
HR high resolution
i. v. in vacuo
LC-MS coupled liquid chromatography-mass spectroscopy
LDA lithium diisopropylamide
m middle (in UV and IR spectra)
m multiplet (in NMR spectra)
MALDI matrix-assisted laser desorption/ionization
MIC minimum inhibitory concentration
min minute(s)
m.p. melting point
MRSA methicillin-resistant *Staphylococcus aureus*
MS mass spectroscopy
NCCLS National Committee for Clinical Laboratory Standards
neg. negative
NMM N-methylmorpholine
NMR nuclear magnetic resonance spectroscopy
p.a. pro analysi
Pd Palladium
Pd—C palladium on carbon
pos. positive
PTFE polytetrafluoroethylene
quant. quantitative
RP-HPLC reverse phase HPLC
RT room temperature
$R_t$ retention time (in HPLC)
s strong (in UV and IR spectra)
s singlet (in NMR spectra)
sat. saturated
TBTU O-(benzotriazol-1-yl)-N,N,N',N'-tetramethyluronium tetrafluoroborate
TCTU O-(1H-6-chlorobenzotriazol-1-yl)-1,1,3,3-tetramethyluronium tetrafluoroborate
TFA trifluoroacetic acid
TFE 2,2,2-trifluoroethanol
THF tetrahydrofuran
TLC thin-layer chromatography
TOF time of flight
UV ultraviolett
vis visible
VRSA vancomycin-resistant *Staphylococcus aureus*
w weak (in UV and IR spectra)
Z, Cbz benzyloxycarbonyl References Concerning the nomenclature of peptides and cyclodepsipeptides, compare:

1. A Guide to IUPAC Nomenclature of Organic Compounds (Recommendations 1993), 1993, Blackwell Scientific publications.
2. Nomenclature and symbolism for amino acids and peptides. Recommendations 1983. IUPAC-IUB Joint Commission on Biochemical Nomenclature, UK. *Biochemical Journal* 1984, 219, 345-373, and cited literature.

General GC-MS, LC-MS, HR-MS, HPLC and Gel Chromatography Methods

Method 1 (TOF-HR-MS): TOF-HR-MS-ESI+ spectra are recorded using a Micromass LCT instrument (capillary voltage: 3.2 KV, cone voltage: 42 V, source temperature: 120° C., desolvation temperature: 280° C.). A syringe pump (from Harvard Apparatus) is used for sample introduction for this purpose. Leucine encephalin (Tyr-Gly-Gly-Phe-Leu) serves as standard.

Method 2 (preparative HPLC): Instrument: Gilson Abimed HPLC; UV detector 210 nm; binary pump system; column: Waters Symmetry-Prep™ $C_{18}$, 7 µm, 300×19 mm; eluent A: 0.2% trifluoroacetic acid in water, eluent B: acetonitrile; flow rate: 25 ml/min; column temperature RT; 0 min 20% B, ramp 0-10 min 70% B, ramp 10-10.1 min 20% B, 15 min 20% B.

Method 3 (gel chromatography on Sephadex LH-20): Gel chromatography is performed without pressure on Sephadex LH-20 (from Pharmacia). Fractions are taken according to UV activity (UV detector for 254 nm, from Knauer) (ISCO Foxy 200 fraction collector), column dimensions: 32×7 cm (1000-100 µmol scale); 30×4 cm (100-10 µmol scale); 25×2 cm (10-1 µmol scale). A column with dimensions 80×30 cm is used for scales from 1 mmol to 11 mmol. In this case, the fractions are collected manually and without upstream UV detector. The fractions are assigned by HPLC (method 9).

Method 4 (preparative HPLC; Kromasil, acetic acid): Instrument: Gilson Abimed HPLC; UV detector 210 nm; binary pump system; column: Kromasil-100A $C_{18}$, 5 µm; 250×20 mm; flow rate: 25 ml/min; eluent A: water/0.25-0.5% acetic acid, eluent B: acetonitrile; gradient: 0-3 min 5% B, 3-30 min 5-100% B, 30-38 min 100% B, then regeneration of the chromatography column.

Method 5 (LC-MS): Instrument: Micromass Quattro LCZ mit HPLC Agilent series 1100; column: Phenomenex Synergi 2μ Hydro-RP Mercury 20 mm×4 mm; eluent A: 1 l of water+ 0.5 ml. of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 6 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 7 (LC-MS): MS instrument type: Micromass ZQ; HPLC instrument type: HP 1100 series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 8 (analytical HPLC): HPLC instrument type: HP 1050 series; UV DAD 1100 series; column: Kromasil $C_{18}$, 60×2 mm, 3.5 μm; eluent A: water/0.5% perchloric acid, eluent B: acetonitrile; gradient: 0-0.5 min 2% B, 0.5-4.5 min 2-90% B, 4.5-9.0 min 90% B, 9.0-9.2 min 90-2% B, 9.2-10.0 min 2% B; flow rate: 0.75 ml/min, oven: 30° C., UV detection 210 nm.

Method 9 (analytical HPLC, Agilent Zorbax $C_8$): Instrument: Agilent 1100 with DAD (G1315B), binary pump (G1312A), autosampler (G1313A), solvent-degasser (G1379A) and column thermostat (G1316A); column: Agilent Zorbax Eclipse XDB-C8 4.6×150×5 mm; eluent A: 0.05% 70% perchloric acid in water; eluent B: acetonitrile; gradient: 0-1 min 10% B, ramp, 4-5 min 90% B, ramp, 5.5 min 10% B; flow rate: 2.00 ml/min; column temperature: 30° C.

Method 10 (gel chromatography on Sephadex LH-20): Gel chromatography is performed without pressure on Sephadex LH-20 (from Pharmacia). Fractions are taken according to UV activity (UV detector for 254 nm, from Knauer) (ISCO Foxy 200 fraction collector), column dimensions: 32×7 cm (1000-100 μmol scale); 30×4 cm (100-10 μmol scale); 25×2 cm (10-1 μmol scale).

Method 11 (preparative Symmetry HPLC): Instrument: Gilson Abimed HPLC; binary pump system; column: SymmetryPrep™$C_{18}$, from Waters, 7 μm; 300 mm×19 mm; eluent A: water/0.2% trifluoroacetic acid, eluent B: acetonitrile; gradient: 0-10 min 15-65% B, then regeneration of the chromatography column; flow rate: 25 ml/min; W detection 210 nm.

Method 12 (preparative Kromasil HPLC): Instrument: Gilson Abimed HPLC; binary pump system; column: Kromasil $C_{18}$, 5 μm, 100 Å, 250×20 mm; eluent A: 0.05% trifluoroacetic acid in water, eluent B: 0.05% trifluoroacetic acid in acetonitrile; gradient: 0-3 min 10% B, ramp, 30-38 min 90% B, 38-45 min 10% B; flow rate: 20 ml/min; UV detection 210 nm.

Method 13 (preparative Waters Symmetry HPLC): Instrument: Gilson Abimed HPLC; binary pump system; column: Waters Symmetry-Prep™ $C_{18}$, 7 μm, 300×19 mm; eluent A: 0.05% trifluoroacetic acid in water, eluent B: 0.05% trifluoroacetic acid in acetonitrile; gradient: 0-3 min 10% B, ramp, 30-38 min 90% B, 38-45 min 10% B; flow rate: 20 ml/min; UV detection 210 nm.

Method 14 (preparative HPLC): Instrument: Gilson Abimed HPLC; binary pump system; column: Waters Symmetry-Prep™ $C_{18}$, 7 μm, 300×19 mm; eluent A: water/0.2% trifluoroacetic acid, eluent B: acetonitrile; gradient: 0-10 min 25-65% B, then regeneration of the chromatography column; flow rate: 25 ml/min; UV detection 210 nm.

Method 15 (Chiral HPLC Daicel Chiralpak): Agilent 1100 HPLC; column: Daicel Chiralpak AD-H 5 μm; 250×20 mm; isocratic: 75% iso-hexane, 25% 2-propanol with 0.2% trifluoroacetic acid and 1% water; flow rate: 1.0 ml/min; oven: 25° C.; UV detector 212 nm.

Method 16 (preparative HPLC): Instrument: Gilson Abimed HPLC; binary pump system; column: YMC ODS-AQ 5 μm, 250×30 mm; eluent A: 0.05% trifluoroacetic acid in water, eluent B: 0.05% trifluoroacetic acid in acetonitrile; gradient: 0-3 min 10% B, ramp, 30-38 min 90% B, 38-45 min 10% B; flow rate: 50 ml/min; UV detector 210 nm.

Method 17 (GC-MS): Instrument: Micromass GCT, GC6890; column: Restek RTX-35MS, 30 m×250 μm×0.25 μm; gradient: 60° C. (maintain for 0.30 min), 50° C./min→120° C., 16° C./min→250° C., 30° C./min→300° C. (maintain for 1.7 min); constant flow rate with helium: 0.88 ml/min; oven: 60° C.; inlet: 250° C.

Method 18 (HPLC): HPLC instrument type: HP 1100 series; UV DAD column: Zorbax Eclipse XBD-C8 (Agilent), 150 mm×4.6 mm, 5 μm; eluent A: 5 ml of $HClO_4$/l of water, eluent B: acetonitrile; gradient: 0-1 min 10% B, 1-4 min 10-90% B, 4-5 min 90% B; flow rate: 2.0 ml/min; oven: 30° C.; UV detection: 210 and 254 nm.

Method 19 (HPLC): column: Kromasil RP-18, 60 mm×2 mm, 3.5 μm; eluent A: 5 ml of $HClO_4$/l of water, eluent B: acetonitrile; gradient: 0 min 2% B, 0.5 min 2% B, 4.5 min 90% B, 9 min 90% B; flow rate: 0.75 ml/min; oven: 30° C.; UV detection: 210 nm.

Method 20 (HPLC): column: Kromasil RP-18, 250 mm×4 mm, 5 μm; eluent A: 5 ml of $HClO_4$/l of water, eluent B: acetonitrile; gradient: 0 min 5% B, 10 min 95% B; flow rate: 1 ml/min; oven: 40° C.; UV detection: 210 nm.

Method 21 (HPLC): column: Kromasil RP-18, 250 mm×4 mm, 5 μm; eluent A: 2 ml of $HClO_4$/l of water, eluent B: acetonitrile; isocratic: 45% B, 55% A; flow rate: 1 ml/min; oven: 40° C.; UV detection: 210 nm.

Method 22 (LC-MS): MS instrument type: Micromass ZQ; HPLC intrument type: HP 1100 series; UV DAD; column: Grom-Sil 120 ODS-4 HE 50×2 mm, 3.0 μm; eluent A: water/0.025% formic acid/l, eluent B: acetonitrile/0.025% formic acid; gradient: 0-2.9 min 0-70% B, 2.9-3.1 min 70-90% B, 3.1-4.5 min 70-90% B; oven: 50° C., flow rate: 0.8 ml/min, UV detection: 210 nm.

Method 23 (HPLC): HPLC instrument type: HP 1050 series; UV DAD 1100 series; column SymmetryPrep™$C_{18}$, from Waters, 50×2.1 mm, 3.5 μm; eluent A: water/0.05% trifluoroacetic acid, eluent B: acetonitrile; gradient: 0-9 min 0-100% B, 9-11 min 100% B, 11-12 min 100-0% B, then regeneration of the chromatography column; oven: 40° C., flow rate: 0.4 ml/min, UV detection: 210 nm.

Method 24 (quantitative $^{19}$F-NMR spectroscopy): approximately 10 mg of accurately weighed sample substance and approximately 20 mg of accurately weighed 1,4-dibromotetrafluorobenzene are dissolved in pyridine and surveyed by $^{19}$F-NMR spectroscopy. δ −74 (TFA) and −132.0 (1,4-dibromotetrafluorobenzene) are integrated and compared. The TFA content is stated as TFA as percentage of the mass of the sample substance.

Method 25 (ion chromatography): Ion chromatography system with suppressor system and conductivity detector; precolumn: A SUPP 4/5 Guard, separating column: A SUPP 5 4.0×250 mm; eluent: 3.2 mM sodium carbonate and 2.4 mM sodium bicarbonate in water; flow rate: 0.7 ml/min. The sample is dissolved in methanol (20% of the final sample volume), treated in an ultrasound bath for 3 min and made up with water. The sample is filtered through an ion-free cellulose acetate filter (Por 0.45 μm) and injected. Quantification versus external standards (0.5 mg/l-10 mg/l).

Starting Compounds

Example 1A

D-Leucyl-N$^1$-4-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate (lysobactin)

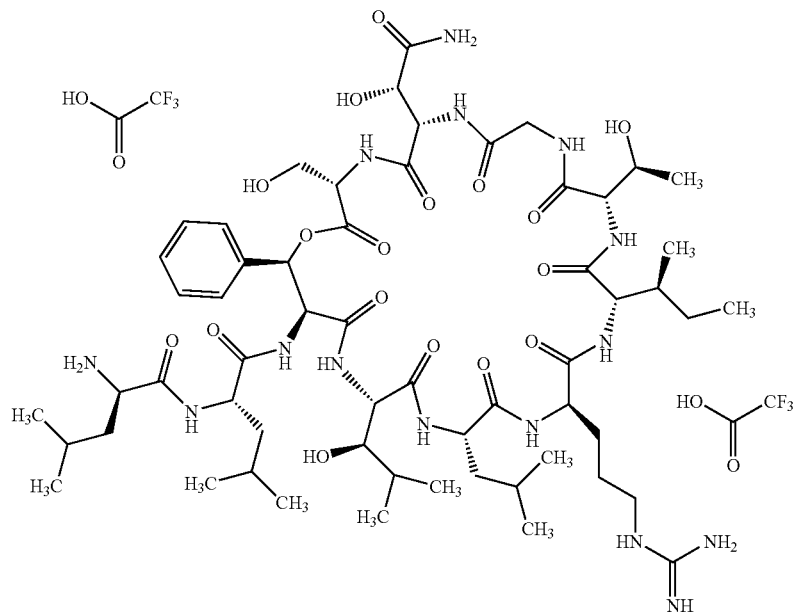

Fermentation:

Culture Medium:

YM: yeast-malt agar: D-glucose (4 g/l), yeast extract (4 g/l), malt extract (10 g/l), 1 litre of Lewatit water. The pH is adjusted to 7.2 before the sterilization (20 minutes at 121° C.).

HPM: mannitol (5.4 g/l), yeast extract (5 g/l), meat peptone (3 g/l).

Working cell bank: the lyophilized strain (ATCC 53042) is grown in 50 ml of YM medium.

Flask fermentation: 150 ml of YM medium or 100 ml of UPM medium in a 1 l Erlenmeyer flask are inoculated with 2 ml of the working cell bank and left to grow at 28° C. on a shaker at 240 rpm for 30-48 hours.

30 l Fermentation: 300 ml of the flask fermentation (HPM medium) are used to inoculate a sterile 30 l nutrient medium solution (1 ml of antifoam SAG 5693/1). This culture is left to grow at 28° C., 300 rpm aerating with sterile air at 0.3 vvm for 21 hours. The pH is kept constant at pH=7.2 with 1M hydrochloric acid. In total, 880 ml of 1M hydrochloric acid are added during the culturing time.

Main culture (200 l): 15×150 ml YM medium in 1 l Erlenmeyer flask are inoculated with 2 ml of the working cell bank and left to grow at 28° C. and 240 rpm on a shaker for 48 hours. 2250 ml of this culture are used to inoculate a sterile 200 l nutrient medium solution (YM) (1 ml of antifoam SAG 5693/1) and left to grow at 28° C., 150 rpm aerating with sterile air at 0.3 vvm for 18.5 hours.

Samples (50 ml) are taken each hour to check the progress of the fermentation. 2 ml of this culture broth are mixed with 1 ml of methanol (0.5% trifluoroacetic acid) and filtered through a 0.45 μm filter. 30 μl of this suspension are analysed by HPLC (method 18 and method 19).

After 18.5 hours, the culture broth of the main culture is separated into supernatant and sediment at 17 000 rpm.

Isolation:

The supernatant (183 l) is adjusted to pH 6.5-7 with concentrated trifluoroacetic acid or sodium hydroxide solution and loaded onto a Lewapol column (OC 1064, 60 l contents). Elution is then carried out with pure water, water/methanol 1:1 and then with pure methanol (with 0.1% trifluoroacetic acid). This organic phase is concentrated in vacuo to a remaining aqueous residue of 11.5 l.

The remaining aqueous phase is bound to silica gel $C_{18}$ and fractionated (MPLC, Biotage Flash 75, 75×30 cm, KP-C18-WP, 15-20 μm, flow rate: 30 ml/min; eluent: acetonitrile/water with 0.1% trifluoroacetic acid; gradient: 10%, 15% and 40% acetonitrile). The 40% acetonitrile phase, which contains the major amount of Example 1A, is concentrated in vacuo and then lyophilized (~13 g). This mixture of solids is separated in 1.2 g portions initially on a preparative HPLC (method 7), then by gel filtration on Sephadex LH-20 (5×70 cm, acetonitrile/water 1:1, in each case with 0.05% trifluoroacetic acid) and a further preparative HPLC (method 20).

This process affords 2250 mg of Example 1A.

The sediment is taken up in 4 l of 4:1 acetone/water, mixed with 2 kg of Celite, adjusted to pH=6 with trifluoroacetic acid, thoroughly stirred and centrifuged. The solvent is evaporated in vacuo, and the residue is freeze dried. The resulting lyophilizate (89.9 g) is taken up in methanol, filtered, concentrated and separated on silica gel (method 21). Example 1A is then purified by gel filtration (Sephadex LH-20, 5×68 cm, water/acetonitrile 9:1 (with 0.05% trifluoroacetic acid), flow rate: 2.7 ml/min, fraction size 13.5 ml) to give the pure substance.

This process affords 447 mg of Example 1A.

HPLC (method 18): $R_t$=6.19 min

MS (ESIpos): m/z=1277 (M+H)$^+$ $^1$H NMR (500.13 MHz, $d_6$-DMSO): δ=0.75 (d, 3H), 0.78 (d, 6H), 0.80 (t, 3H), 0.82 (d, 3H), 0.90 (d, 3H), 0.91 (d, 3H), 0.92 (d, 3H), 0.95 (d, 3H), 0.96 (d, 3H), 1.05 (m, 1H), 1.19 (d, 3H), 1.25 (m, 2H), 1.50 (m, 4H), 1.51 (m, 2H), 1.55 (m, 1H), 1.61 (m, 1H), 1.65 (m, 1H), 1.84 (m, 1H), 1.85 (m, 1H), 1.86 (m, 1H), 1.89 (m, 1H), 1.95 (m, 1H), 2.75 (m, 2H), 3.40 (m, 1H), 3.52 (m, 2H), 3.53 (dd, 1H), 3.64 (m, 2H), 3.66 (m, 1H), 3.68 (dd, 1H), 3.73 (m, 2H), 4.00 (dd, 1H), 4.02 (br., 1H), 4.13 (br., 1H), 4.32 (dd, 1H), 4.39 (t, 1H), 4.55 (m, 1H), 4.75 (dd, 1H), 5.19 (t, 1H), 5.29 (d, 1H), 5.30 (br., 1H), 5.58 (m, 2H), 6.68 (m, 3H), 6.89 (d, 1H), 6.93 (m, 3H), 6.94 (br., 1H), 6.98 (d, 1H), 7.12 (br., 1H), 7.20 (br., 2H), 7.23 (m, 2H), 7.42 (m, 2H), 7.54 (d, 1H), 7.58 (d, 1H), 8.32 (br., 1H), 9.18 (br., 1H), 9.20 (m, 2H), 9.50 (br., 1H).

$^{13}$C-NMR (125.77 MHz, d$_6$-DMSO): δ=10.3, 15.3, 19.0, 19.2, 19.6, 20.0, 20.9, 22.0, 22.4, 23.0, 23.2, 24.3, 24.4, 25.0, 25.4, 26.0, 27.8, 30.9, 35.4, 39.5, 40.8, 40.9, 41.6, 44.1, 51.5, 52.7, 55.9, 56.2, 56.4, 57.9, 58.8, 60.2, 61.1, 62.6, 70.1, 71.6, 71.7, 75.5, 128.1, 128.6, 136.7, 156.8, 168.2, 170.1, 170.4, 171.2, 171.5, 171.9, 172.2, 172.4, 173.7.

The assignment of the signals took place in accordance with the assignment described in the literature (T. Kato, H. Hinoo, Y. Terui, *J. Antibiot.*, 1988, 61, 719-725).

Example 2A

De(1-D-leucyl-2-L-leucyl)lysobactin bistrifluoroacetate (Edman$^{2.0}$ Degradation Product)

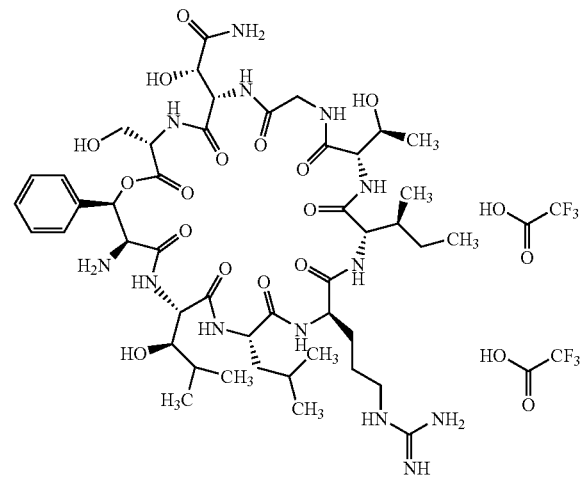

Lysobactin bistrifluoroacetate (60.0 g, 39.88 mmol) is dissolved in pyridine ((840 ml) under an argon atmosphere. Then phenyl isothiocyanate (32.35 g, 239.28 mmol, 6 equivalents) is added, and the reaction mixture is stirred at 37° C. for 7 h. The solvent is distilled off in a rotary evaporator at a bath temperature of 40° C. The residue is mixed with methyl tert-butyl ether (1400 ml) and stirred vigorously for 30 min. It is then filtered with suction through a glass frit (pore width 3, 13 cm diameter). The intermediate product (Edman$^{0.5}$ degradation product) is isolated in a crude yield of 72 g and reacted further without workup.

For this purpose, the crude product is dissolved in trifluoroacetic acid (1026 ml) under an argon atmosphere and stirred at RT for 30 min. The solution is then concentrated in a rotary evaporator in vacuo at a bath temperature of 20° C. The residue is taken up in methyl tert-butyl ether (1400 ml) and stirred vigorously until a powdery amorphous solid is produced. This is filtered off in vacuo on a frit (pore width 3, 18 cm diameter). The solid is then stirred with diethyl ether (1400 ml) and again filtered off. The same procedure is repeated with 2 portions of dichloromethane (900 ml each). The crude product is dried in vacuo. 58 g of crude de(1-D-leucyl)lysobactin bistrifluoroacetate (Edman$^{1.0}$ degradation product) are obtained.

The crude product is dissolved without further workup in pyridine (1080 ml) under an argon atmosphere. Then phenyl isothiocyanate (107 g, 0.80 mol, 20 equivalents) is added and the reaction mixture is stirred at 37 to 40° C. for 7 h. The solvent is then distilled off in a rotary evaporator at a bath temperature of 40° C. The residue is mixed with methyl tert-butyl ether (1400 ml) and stirred vigorously. It is then filtered off with suction on a glass frit (pore width 3, 13 cm diameter). The intermediate product (Edman$^{1.5}$ degradation product) is isolated in a crude yield of 65 g and, after drying under oil pump vacuum, directly dissolved in trifluoroacetic acid (1240 ml) under an argon atmosphere and stirred at RT for 30 min. The solution is then concentrated in a rotary evaporator in vacuo at a bath temperature of 20° C. The residue is taken up in methyl tert-butyl ether (1400 ml) and stirred vigorously until a powdery amorphous solid is produced. This is filtered off on a frit (pore width 3, 18 cm diameter) in vacuo. The solid is then stirred firstly with diethyl ether (1400 ml) and then with dichloromethane (1400 ml) and filtered off each time. 55 g of the crude product are obtained. It is purified by preparative HPLC (method 14). 28.55 g (56% of theory) of the title compound are obtained.

HPLC/UV-Vis (method 23): R$_t$=4.71 min, λ$_{max}$ (qualitative)=220 nm (s), 255-270 (w).

LC-MS (method 22): R$_t$=1.65 min;

MS (ESIpos.): m/z (%)=526 (100) [M+2H]$^{2+}$, 1051 (15) [M+H]$^+$.

Example 3A

Methyl (2Z)-2-{[(benzyloxy)carbonyl]amino}-3-(6-trifluoromethylpyridin-3-yl)acrylate

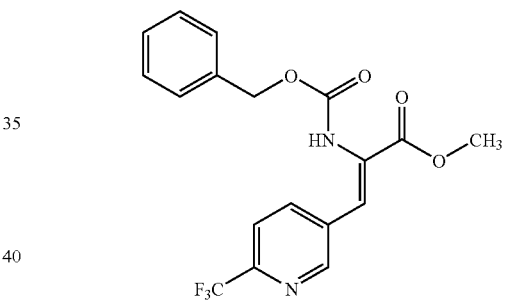

6-Trifluormethylpyridine-3-carbaldehyde (4.85 g, 27.70 mmol) and methyl {[(benzyloxy)carbonyl]amino} (dimethoxyphosphoryl)acetate (9.17 g, 27.70 mmol, 1.0 equivalent) are dissolved in THF (70 ml) and cooled to −70° C. At −70° C., N,N,N,N-tetramethylguanidine (6.38 g, 55.39 mmol, 6.95 ml, 2.0 equivalents) is slowly added dropwise and then stirred at −70° C. for 4 h and subsequently at RT for 12 h. The reaction mixture is concentrated and then extracted from water with ethyl acetate (2×100 ml), and the combined organic phases are washed with saturated brine and dried over sodium sulphate. The crude product after concentration in vacuo is chromatographed (silica gel, eluent: toluene then toluene/ethyl acetate 10:1). 6.93 g (66% of theory) of the title compound are obtained.

HPLC/UV-Vis (method 8): R$_t$=4.60 min.

HPLC/UV-Vis (method 9): R$_t$=4.54 min.

$^1$H-NMR (400 MHz, d$_6$-DMSO): δ=3.74 (s, 3H, OMe), 5.10 (s, 2H, CH$_2$), 7.27 (s, 1H, PyrH), 7.33-7.38 (m, 5H, ArH), 7.94 (d, J=8.5 Hz, 1H, PyrH), 8.27 (d, J=8.5 Hz, 1H, PyrH), 8.93 (s, 1H, β-CH), 9.51 (s, 1H, NH).

LC-MS (method 7): R$_t$=2.44 min; MS (ESIpos.): m/z (%)=381 (100) [M+H]$^+$; MS (ESIneg.): m/z (%)=379 (100) [M−H]$^-$.

HR-TOF-MS (method 1): C$_{18}$H$_{16}$N$_2$O$_4$F$_3$ [M+H]$^+$ calc. 381.1062, found 381.1065.

Example 4A

N-[(Benzyloxy)carbonyl]-3-(6-trifluoromethylpyridin-3-yl)-L-alanine methyl ester

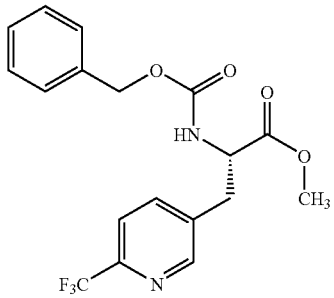

The compound from Example 3A (10.15 g, 26.69 mmol) is dissolved in methanol p.a. (100 ml). Using a needle, argon is passed through for about 5 min and then (+)-1,2-bis[(2S,5S) diethylphospholano]benzene(cyclooctadiene)rhodium(I)triflate (289 mg, 400 µmol, 0.015 equivalent) is added. Hydrogenation is carried out under a pressure of 4 bar of hydrogen and at RT for 12 h. Then filtration through kieselguhr (methanol) is followed by concentration of the eluate. The crude product is chromatographed (silica gel, eluent: toluene/ethyl acetate 5:1). 9.9 g (97% of theory) of the title compound are obtained.

$[\alpha]^{20}_{Na}$=−24° (c=0.093 in methanol).

HPLC/UV-Vis (method 8): $R_t$=4.50 min.

HPLC/UV-Vis (method 9): $R_t$=4.49 min.

$^1$H-NMR (400 MHz, $d_6$-DMSO): δ=2.99 (dd, J=3.5, 11.0 Hz, 1H, β-CH), 3.22 (dd, J=3.5, 11.0 Hz, 1H, β-CH), 3.66 (s, 3H, OMe), 4.40 (m, 1H, α-CH), 4.97 (s, 2H, CH$_2$), 7.23 (m, 2H), 7.29-7.33 (m, 3H), 7.83 (d, J=6.5 Hz, 1H), 7.93-7.98 (m, 2H), 8.65 (s, 1H, NH).

LC-MS (method 7): $R_t$=2.40 min; MS (ESIpos.): m/z (%)=383 (100) [M+H]$^+$; MS (ESIneg.): m/z (%)=273 (100), 381 (50) [M−H]$^−$.

HR-TOF-MS (method 1): $C_{18}H_{18}N_2O_4F_3$ [M+H]$^+$ calc. 383.1219, found 383.1223.

Example 5A 3-(6-Trifluoromethylpyridin-3-yl)-L-alanine methyl ester

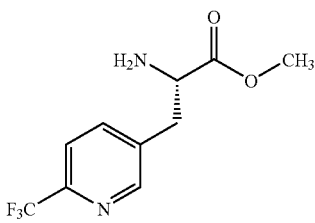

The compound from Example 4A (9.90 g, 25.89 mmol) is dissolved in methanol (100 ml). Using a needle, argon is passed through for about 5 min and then Pd on carbon (10%, 990 mg) is added. Hydrogenation is carried out under a pressure of 4 bar and at RT for 12 h. Then filtration through kieselguhr is followed by concentration and drying under oil pump vacuum.

Yield: 5.8 g (90% of theory) of the title compound.

$[\alpha]^{19.9}_{Na}$=+3° (c=0.186 in methanol).

HPLC/UV-Vis (method 8): $R_t$=3.34 min.

HPLC/UV-Vis (method 9): $R_t$=3.22 min.

IR $\nu_{max}$ (NaCl, cm$^{-1}$): 3415, 1734, 1339, 1136, 1087.

$^1$H-NMR (500 MHz, $d_6$-DMSO): δ=2.85 (dd, J=5.5, 13.5 Hz, 1H, β-CH), 3.01 (dd, J=5.5, 13.5 Hz, 1H, β-CH), 3.61 (s, 3H, OMe), 3.63-3.69 (m, 1H, α-CH), 7.82 (d, J=7.5 Hz, 1H), 7.93 (d, J=7.5 Hz, 1H), 8.61 (s, 1H).

LC-MS (method 7): $R_t$=1.74 min; MS (ESIpos.): m/z (%)=249 (100) [M+H]$^+$.

HR-TOF-MS (method 1): $C_{12}H_{15}N_3O_2F_3$ [M+CH$_3$CN+H]$^+$ calc. 290.1116, found 290.1122.

Example 6A

N-(tert-Butoxycarbonyl)-3-(tert-butyl)-D-alanyl-3-(6-trifluoromethylpyridin-3-yl)-L-alanine methyl ester

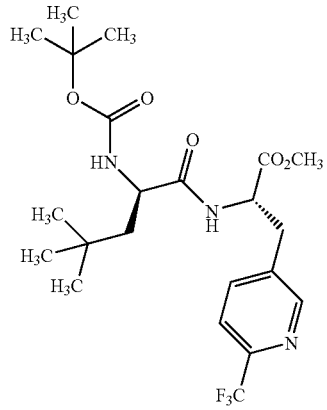

N-Methylmorpholine (12.92 g, 127.72 mmol, 14.04 ml, 5 equivalents) and HATU (9.71 g, 25.54 mmol, 1 equivalent) are added slowly to a solution of the compound from Example 5A (6.34 g, 25.54 mmol) and N-(tert-butoxycarbonyl)-3-tert-butyl-D-alanine (6.27 g, 25.54 mmol, 1.0 equivalent) in dry DMF (240 ml) at −30° C. The reaction mixture warms slowly (about 3 h) to RT, with complete conversion being observed by means of HPLC (method 9). Potassium dihydrogenphosphate (34.76 g, 255.44 mmol, 10 equivalents) is added, and the reaction mixture is stirred for 20 min and then filtered, diluted with ethyl acetate and washed with saturated aqueous sodium bicarbonate solution (10 ml). The organic phase is dried with sodium sulphate, filtered and concentrated. The crude product is purified by flash chromatography (silica gel, 10:1 to 2:1 cyclohexane/ethyl acetate gradient), resulting in 9.74 g (73% of theory) of the title compound.

$[\alpha]^{19.9}_{Na}$=+7.0° (c=0.044 in methanol).

HPLC/UV-Vis (method 8): $R_t$=4.89 min.

HPLC/UV-Vis (method 9): $R_t$=4.75 min.

IR $\nu_{max}$ (NaCl, cm$^{-1}$): 2959, 1742, 1655, 1520, 1336, 1160, 1136, 1087, 1050, 1027.

$^1$H-NMR (500 MHz, $d_6$-DMSO): δ=0.74 (s, 9H, tBu), 0.97-1.00 (m, 1H, β-CH2), 1.20-1.25 (m, 1H, β-CH2), 1.35 (s, 9H, OtBu), 2.99-3.05 (m, 1H, β-CH2), 3.23-3.26 (m, 1H, β-CH2), 3.66 (s, 3H, OMe), 3.94 (m, 1H, α-CH), 4.60 (m, 1H, α-CH), 6.82 (d, J=8.5 Hz, 1H, NH), 7.78 (d, J=8.0 Hz, 1H, PyrH), 7.94 (d, J=8.0 Hz, 1H, PyrH), 8.34 (d, J=8.5 Hz, 1H, NH), 8.64 (s, 1H, PyrH).

LC-MS (method 7): $R_t$=2.67 min; MS (ESIpos.): m/z (%)=476 (100), [M+H]$^+$; MS (ESIneg.): m/z (%)=400 (80), 474 (40) [M−H]$^−$.

HR-TOF-MS (method 1): $C_{22}H_{33}N_3O_5F_3$ [M+H]$^+$ calc. 476.2372, found 476.2364.

Example 7A

N-tert-Butoxycarbonyl-3-tert-butyl-D-alanyl-3-(6-trifluoromethylpyridin-3-yl)-L-alanine

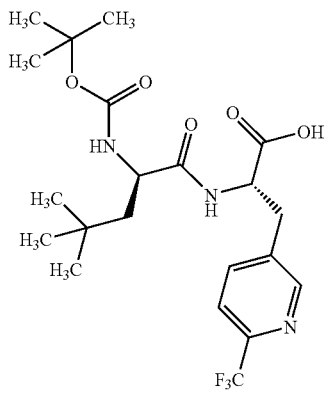

A solution of lithium hydroxide hydrate (1.16 g, 2.5 equivalents, 48.37 mmol) in water (20 ml) is added to a solution of the compound from Example 6A (9.2 g, 1.0 equivalent, 19.35 mmol) in THF (360 ml) and water (100 ml) at −20° C. The reaction mixture warms (about 1.5 h) to +15° C., with complete conversion being observed by means of HPLC (method 9). For working up, potassium dihydrogenphosphate (26.33 g, 10 equivalents, 193.5 mmol) is added (about pH 7). The reaction mixture is filtered and concentrated in vacuo. The crude product is purified by gel chromatography (method 10, mobile phase methanol/acetone 4:1), resulting in 4.72 g (53% of theory) of product.

$[\alpha]^{20}{}_{Na}$=+51.3° (c=0.402 in methanol).

HPLC/UV-Vis (method 8): $R_t$=4.63 min.

HPLC/UV-Vis (method 9): $R_t$=4.55 min.

IR $\nu_{max}$ (NaCl, cm$^{-1}$): 3305, 2959, 1663, 1519, 1336, 1173, 1134, 1086.

$^1$H-NMR (500 MHz, d$_6$-DMSO): δ=0.77 (s, 9H, tBu), 1.06-1.13 (m, 1H, β-CH2), 1.23-1.26 (m, 1H, β-CH2), 1.34 (s, 9H, OtBu), 3.01 (t$_{app}$, J=11.0 Hz, 1H, β-CH2), 3.23 (br d, J=11.0 Hz, 1H, β-CH2), 3.94 (t, J=8.0 Hz, 1H, α-CH), 4.42 (br s, 1H, α-CH), 6.90 (d, J=8.5 Hz, 1H, NH), 7.74 (d, J=7.5 Hz, 1H, PyrH), 7.86 (d, J=7.5 Hz, 1H, PyrH), 8.00 (br s, 1H, NH), 8.56 (s, 1H, PyrH).

LC-MS (method 7): $R_t$=2.42 min; MS (ESIpos.): m/z (%)=406 (100), 462 (85) [M+H]$^+$; MS (ESIneg.): m/z (%)=460 (100) [M−H]$^-$.

HR-TOF-MS (method 1): C$_{21}$H$_{31}$N$_3$O$_5$F$_3$ [M+H]$^+$ calc. 462.2216, found 462.2203.

Example 8A

N-tert-Butoxycarbonyl-3-tert-butyl-D-alanyl-3-(6-trifluoromethylpyridin-3-yl)-L-alanylde(1-D-leucyl-2-L-leucyl)lysobactin trifluoroacetate

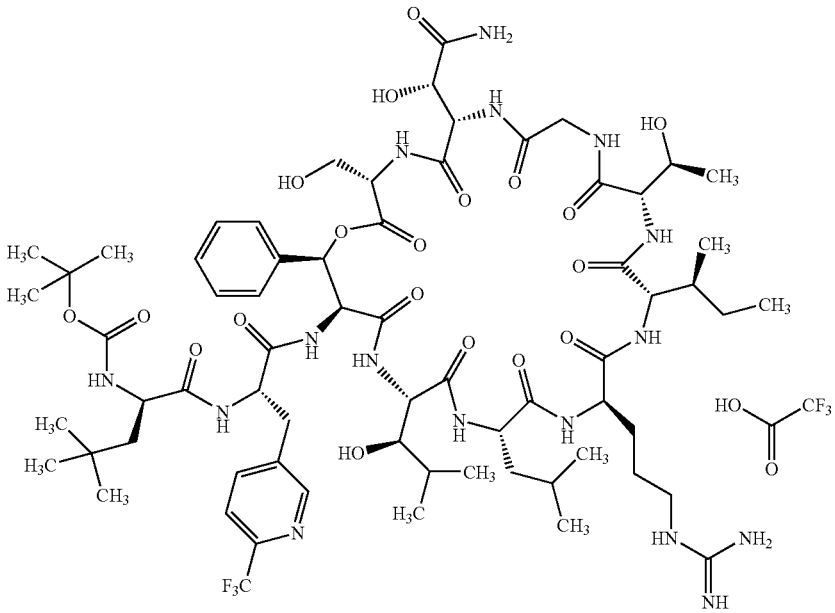

N-Methylmorpholine (2.77 g, 3.01 ml, 5 equivalents, 27.38 mmol) and HATU (4.37 g, 2.1 equivalents, 11.50 mmol) are added slowly to a solution of the compound from Example 2A (7.00 g, 1.0 equivalent, 5.48 mmol) and Example 7A (3.03 g, 1.2 equivalents, 6.57 mmol) in dry DMF (119 ml) at −30° C. The reaction mixture warms slowly (about 1 h) to RT, with complete conversion being observed by means of HPLC/UV-Vis (method 9). The reaction is quenched with potassium dihydrogenphosphate (7.45 g, 10.0 equivalents, 54.76 mmol). The reaction mixture is purified by gel chromatography (method 10, mobile phase methanol/acetone 4:1), resulting in 12.63 g (quant.) of product.

HPLC/UV-Vis (method 8): $R_t$=4.78 min.

HPLC/UV-Vis (method 9): $R_t$=4.35 min.

LC-MS (method 7): $R_t$=2.28 min; MS (ESIpos.): m/z (%)=697 (100) [M+2H]$^{2+}$, 1493 (15) [M+H]$^+$; MS (ESIneg.): m/z (%)=745 (100) [M−2H]$^{2-}$, 1491 (5) [M−H]$^-$.

HR-TOF-MS (method 1): C$_{67}$H$_{104}$N$_{16}$O$_{19}$F$_3$ [M+H]$^+$ calc. 1493.7616, found 1493.7594.

Example 9A and Example 10A (2S)-N-(tert-Butoxycarbonyl)-3-trimethylsilyl)alanine and (2R)-N-(tert-butoxycarbonyl)-3-(trimethylsilyl)alanine Synthesis takes place as described by M. Merget, K. Günther, M. Bernd, E. Günther, R. Tacke, *J. Organomet. Chem.* 2001 628, 183-194. The enantiomers are separated by preparative HPLC on a chiral phase: Gilson Abimed HPLC; column: Daicel Chiralpak AD-H 5 μm; 250×20 mm; eluent A: iso-hexane, eluent B: 0.2% acetic acid/1% water/2-propanol; isocratic; flow rate: 15 ml/min; UV detector 212 nm. The isomers are assigned by HPLC comparison with an authentic sample of N-(tert-butoxycarbonyl)-L-3-trimethylsilylalanine (2R compound, Mercachem AMR 39.260).

Example 9A

N-(tert-Butoxycarbonyl)-D-3-trimethylsilylalanine (2S compound)

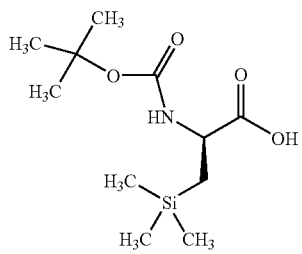

Chiral HPLC (method 15): $R_t$=4.16 min, e.e. >99%. $[\alpha]_D^{20}$=+1.1 (c=0.83 in methanol)

Example 10A

N-(tert-Butoxycarbonyl)-L-3-trimethylsilylalanine (2R compound)

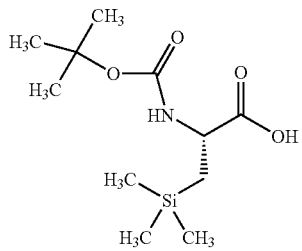

Chiral HPLC (method 15): $R_t$=9.27 min. e.e. >99%. $[\alpha]_D^{20}$=−1.6 (c=0.66 in methanol)

Example 11A

Methyl N-(tert-butoxycarbonyl)-3-(pyridin-3-yl)-L-alaninate

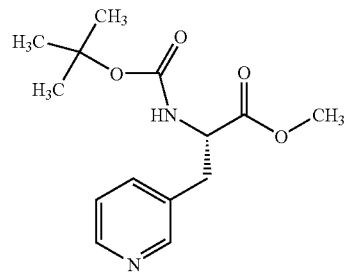

Preparation takes place in analogy to B. Neises, W. Steglich, *Org. Synth.* 1985, 63, 183-187.

(2S)-N-(tert-Butoxycarbonyl)-3-(pyridin-3-yl)alanine (25.00 g, 93.88 mmol) is dissolved in 300 ml of dichloromethane under argon. Methanol (11.4 ml, 9.02 g, 281 mmol, 3 equivalents) and a small crystal of DMAP are added. The mixture is then cooled to 0° C. EDC (19.80 g, 103 mmol, 1.1 equivalents) is added. After 5 min., the ice bath is removed and the mixture is stirred at RT for 1 h. It is then concentrated in vacuo, and the residue is mixed with ethyl acetate and extracted with saturated sodium bicarbonate solution. The aqueous phase is back-extracted once with ethyl acetate, and then the combined organic phases are washed with 0.5 M citric acid and then once again with saturated sodium bicarbonate solution. The organic phase is dried over sodium sulphate, filtered and concentrated in vacuo. A clear oil remains and crystallizes on drying under oil pump vacuum. Yield: 23.60 g (90% of theory).

HPLC/UV-Vis (method 9): $R_t$=3.28 min.

LC-MS (method 7): $R_t$=1.21 min, MS (ESIpos.): m/z (%)=281 (100) [M+H]⁺.

¹H-NMR (400 MHz, d₆-DMSO): δ=1.30 (s, 9 Hz, 2.86 (m, 1H), 3.04 (m, 1H), 3.63 (s, 3H), 4.22 (m, 1H), 7.28-7.39 (m, 2H), 7.69 (d, 1H), 8.43 (m, 2H).

Example 12A 3-(pyridine-3-yl)-L-alanine methyl ester bistrifluoroacetate

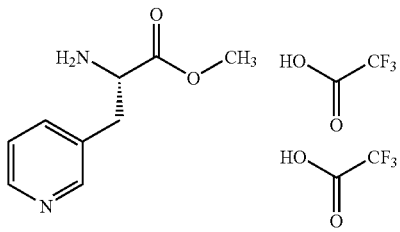

The compound from Example 11A (11.8 g, 42.09 mmol) is dissolved in trifluoroacetic acid in dichloromethane (160 ml; 30% strength solution) and stirred at RT for 30 min. It is then concentrated in vacuo. The residue is taken up in a little water and lyophilized. The lyophilizate is then mixed with toluene and concentrated in vacuo. The product is finally dried to constant weight under oil pump vacuum. Yield: 17.15 g (quant.).

HPLC/UV-Vis (method 9): $R_t$=0.88 min.

LC-MS (method 7): $R_t$=0.46 min, MS (ESIpos.): m/z (%)=181 (100) [M+H]⁺.

¹H-NMR (400 MHz, d₆-DMSO): δ=2.79 (dd, 1H), 2.92 (dd, 1H), 3.60 (s, 3H), 3.63 (m, 1H), 7.30 (m, 1H), 7.62 (d, 1H), 8.41 (m, 2H).

Example 13A

Methyl N-(tert-butoxycarbonyl)-3-(trimethylsilyl)-D-alanyl-3-(pyridin-3-yl)-L-alaninate

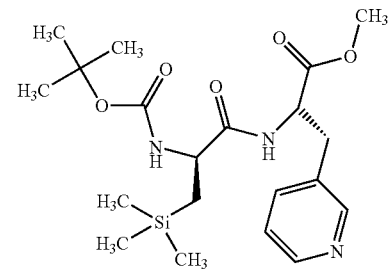

The compound from Example 9A (10.31 g, 39.4 mmol) and the compound from Example 12A (16.10 g, 39.4 mmol, 1 equivalent) are dissolved in DMF (186 ml) at 0° C. Then N-methylmorpholine (17.34 ml, 16.00 g, 4 equivalents) and HATU (22.49 g, 59.16 mmol, 1.5 equivalents) are added. The mixture is stirred at RT for two hours. tert-Butyl methyl ether is added, and the mixture is washed with saturated sodium carbonate solution. The aqueous phase is back-extracted once with tert-butyl methyl ether, and then the combined organic phases are washed with 1 M aqueous citric acid and again with saturated sodium carbonate solution, dried over sodium sulphate, filtered and concentrated in vacuo. Filtration through silica gel is carried out (cyclohexane/ethyl acetate 2:1). Yield: 14.1 g (84% of theory).

HPLC/UV-Vis (method 9): $R_t$=3.91 min.

LC-MS (method 7): $R_t$=1.90 min, MS (ESIpos.): m/z (%)=424 (100) [M+H]$^+$.

$^1$H-NMR (400 MHz, $d_6$-DMSO): δ=−0.09 (s, 9H), 0.56-0.75 (m, 2H), 1.47 (s, 9H), 2.90 (dd, 1H), 3.09 (dd, 1H), 3.62 (s, 3H), 3.98 (m, 1H), 4.49 (m, 1H), 6.68 (d, 1H), 7.26 (dd, 1H), 7.61 (m, 1H), 8.20 (d, 1H), 8.40 (m, 2H).

Example 14A

N-(tert-Butoxycarbonyl)-3-(trimethylsilyl)-D-alanyl-3-(pyridin-3-yl)-L-alanine

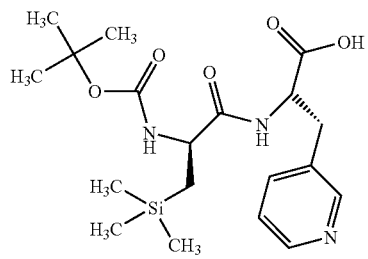

The compound from Example 13A (7.4 g, 17.56 mmol) is taken up in THF/water (6:4) and cooled to 0° C., and lithium hydroxide monohydrate (1.47 g, 35.13 mmol, 2 equivalents) is added. The mixture is stirred at 0° C. After one hour, a further equivalent (0.74 g) of lithium hydroxide monohydrate is added, and stirring is continued for one hour. Most of the THF is distilled off in vacuo, and the aqueous phase is washed with two portions of methyl tert-butyl ether and then adjusted to pH 4 by adding citric acid. A solid precipitates. It is extracted with three portions of ethyl acetate, the solid dissolving. The combined organic phases are dried over sodium sulphate, filtered and concentrated. The crude product is purified by gel chromatography (method 3, mobile phase: methanol). Yield: 6.67 g (93% of theory).

HPLC/UV-Vis (method 9): $R_t$=3.73 min.

LC-MS (method 7): $R_t$=1.68 min, MS (ESIpos.): m/z (%)=410 (40) [M+H]$^+$.

$^1$H-NMR (300 MHz, $d_6$DMSO): δ=−0.090 (s, 9H), 0.56-0.75 (m, 2H), 1.35 (s, 9H), 2.90 (dd, 1H), 3.09 (dd, 1H), 3.98 (m, 1H), 4.41 (m, 1H), 6.70 (d, 1H), 7.26 (dd, 1H), 7.60 (m, 1H), 8.00 (d, 1H), 8.37 (m, 2H).

Example 15A

N-(tert-Butoxycarbonyl)-3-(trimethylsilyl)-D-alanyl-3-(pyridin-3-yl)-L-alanyl-de(1-D-leucyl-2-L-leucyl) lysobactin trifluoroacetate

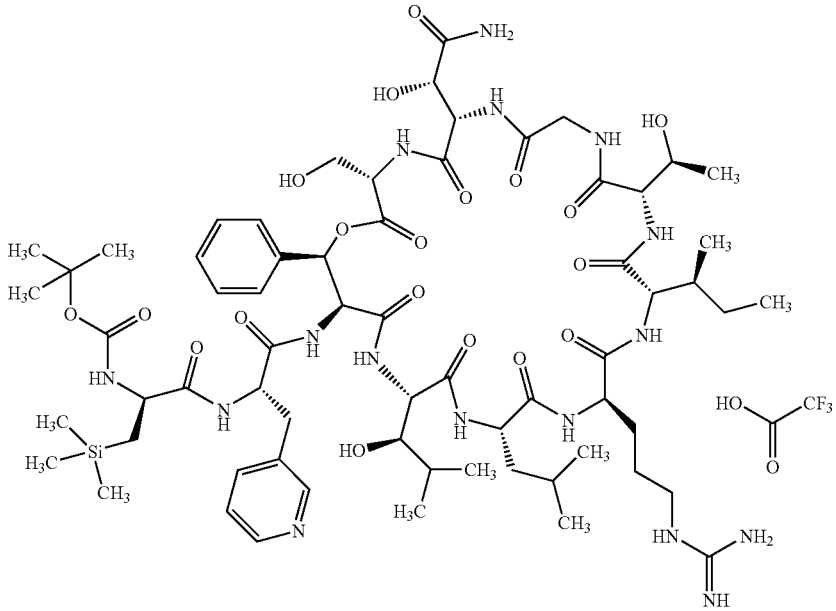

The compound from Example 2A (3.00 g, 2.35 mmol) and the compound from Example 14A (1.44 g, 3.52 mmol, 1.5 equivalents) are dissolved in DMF (50 ml) and cooled to 0° C. Then firstly 4.7 ml (4.7 mmol, 2 equivalents) of a 1 M solution of 4-methylmorpholine in DMF are added. Immediately thereafter, HATU (1.52 g, 3.99 mmol, 1.7 equivalents) is added and the mixture is stirred at 0° C. for 15 min. Then a further 4.7 ml (4.7 mmol, 2 equivalents) of the 1 M solution of 4-methylmorpholine in DMF are added dropwise. The mixture is then stirred at RT for 2 h. The crude product is subjected to gel chromatography (method 3). The product is reacted further without final purification. Yield: 3.6 g (82% of theory).

HPLC (method 9): $R_t$=3.90 ml.

LC-MS (method 7): $R_t$=2.00 min. MS (ESIpos.): m/z (%)=721.8 (100) [M+2H]$^{2+}$; 1442.1 (5) [M+H]$^+$.

Alternative process: The compound from Example 2A (14.00 g, 10.95 mmol) and the compound from Example 14A (5.38 g, 13.14 mmol, 1.2 equivalents) are dissolved in DMF (280 ml) and cooled to −20° C. Then N-methylmorpholine (5.54 g, 6.02 ml, 5 equivalents) is added and subsequently HATU (6.66 g, 17.52 mmol, 1.6 equivalents). The mixture is slowly warmed to RT and stirred overnight (about 16 h). Then potassium dihydrogenphosphate (14.91 g, 10 equivalents) is added with stirring, and stirring is continued for 30 minutes. The crude product is subjected to gel chromatography (method 3, mobile phase: methanol). The product is reacted further without final purification. Yield: 14.35 g (61% of theory).

Example 16A 2,2-Dimethyl-1-butanal

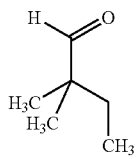

2,2-Dimethyl-1-butanol (4.0 g, 39 mmol) is dissolved in dichloromethane (136 ml), and aluminium oxide (7.98 g, 78 mmol, 2 equivalents) and pyridinium chlorochromate (16.88 g, 78 mmol, 2 equivalents) are added. The mixture is stirred at RT for 1 h and then filtered through a layer of silica gel. The filtrate is cautiously concentrated, and the residue is distilled under atmospheric pressure (boiling point: 102° C. (990 mbar)). Yield: 2.97 g (75% of theory).

GC-MS (method 17): $R_t$=2.21 min, MS (ESIpos.): m/z (%)=99.9 (5) [M]$^+$;

$^1$H NMR (400 MHz, CDCl$_3$) δ 0.83 (t, 3H), 1.03 (s, 6H), 1.51 (q, 2H), 9.42 (s, 1H).

Example 17A

Methyl (2Z)-2-{[(benzyloxy)carbonyl]amino}-4,4-dimethylhex-2-enoate

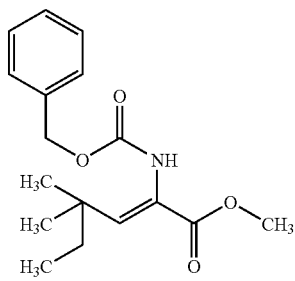

The compound from Example 16A (2.55 g, 25.46 mmol) and methyl {[(benzyloxy)carbonyl]-amino}(dimethoxyphosphoryl)acetate (8.43 g, 25.46 mmol) are dissolved in 50 ml of THF and cooled to 0° C. N,N,N',N'-Tetramethylguanidine is added dropwise, and the mixture is then stirred, firstly at 0° C. for 15 min and then at RT for 5 days. About 20 g of silica gel are added to the mixture, which is concentrated and chromatographed (Biotage 40M, ZIF-SIM, silica gel, cyclohexane/ethyl acetate 87:13). Yield: 1.20 g (13% of theory).

HPLC (method 9): $R_t$=3.71 min.

MS (DCI): m/z (%)=323.3 (100) [M+NH$_4$].

$^1$H-NMR (400 MHz, CDCl$_3$): δ=0.83 (m, 31), 1.13 (s, 6H), 1.49 (q, 2H), 3.75 (br s, 3H), 5.72 (br s, 1H), 6.58 (br s, 1H), 5.12 (s, 2H), 7.36 (m, 5H).

Example 18A

Methyl N-[(benzyloxy)carbonyl]-4,4-dimethyl-D-norleucinate

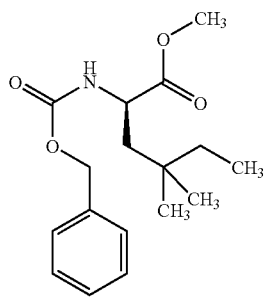

The compound from Example 17A (1.2 g, crude product, 3.26 mmol) is dissolved in ethanol p.a. (60 ml). Using a needle, argon is passed through for about 5 min, and then (+)-1,2-bis[(2R,5R)diethylphospholano]benzene(cyclooctadiene)rhodium(I)triflate (28 mg, 0.04 mmol, 0.012 equivalent) is added and dissolved in an ultrasound bath. Hydrogenation is carried out under a pressure of 3 bar of hydrogen and at RT for 24 h. The mixture is concentrated and chromatographed (Biotage 25M silica gel, cyclohexane/ethyl acetate 9:1). Yield: 920 mg (92% of theory).

HPLC (method 9): $R_t$=4.96 min.

LC-MS (method 7): $R_t$=2.76 min; MS (ESIpos.): m/z (%)=308 (25) [M+H]$^+$.

$^1$H-NMR (400 MHz, CDCl$_3$): δ=0.80 (t, 3H), 0.86 (s, 6H), 1.29 (q, 2H), 1.41 (dd, 1H), 1.73 (dd, 1H), 3.72 (s, 3H), 4.40 (m, 1H), 5.02 (d, 1H), 5.11 (m, 2H), 7.35 (m, 5H).

Example 19A

N-[(Benzyloxy)carbonyl]-4,4-dimethyl-D-norleucine

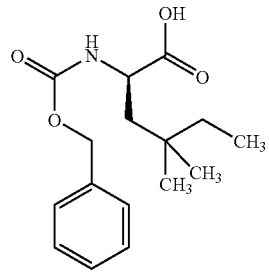

The compound from Example 18A (915 mg, 2.98 mmol) is dissolved in THF (12 ml). The solution is cooled to 0° C. and then 3.7 ml (7.4 mmol, 2.5 equivalents) of a 2 M solution of lithium hydroxide monohydrate in water are added and stirred vigorously for 1 h. Citric acid (1 M) is then added dropwise until the reaction is acidic, and the mixture is extracted with ethyl acetate. The organic extract is dried over sodium sulphate, concentrated and chromatographed (method 16). Yield: 434 mg (50% of theory).

HPLC (method 9): $R_t$=4.54 min.

LC-MS (method 7): $R_t$=2.44 min, MS (ESIpos.): m/z (%)=294 (20) [M+H]$^+$.

$^1$H-NMR (400 MHz, d$_6$-DMSO): δ=0.80 (t, 3H), 0.83 (s, 6H), 1.21 (q, 2H), 1.53 (dd, 1H), 1.60 (dd, 1H), 3.99 (m, 1H), 5.02 (s, 2H), 7.35 (m, 5H), 7.58 (d, 2H), 12.52 (br s, 1H).

Example 20A

Methyl N-[(benzyloxy)carbonyl]-4,4-dimethyl-D-norleucyl-3-(pyridin-3-yl)-L-alaninate

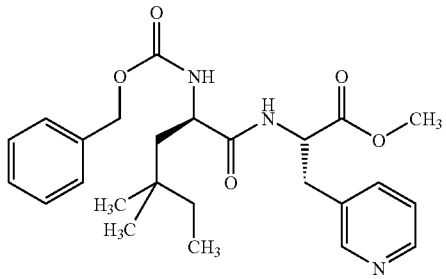

The compound from Example 19A (430 mg, 1.47 mmol) and the compound from Example 12A (809 mg, 1.47 mmol, 1 equivalent) are dissolved in DMF (5 ml) at 0° C. and then 4-methylmorpholine (644 µl, 5.86 mmol, 4 equivalents) and HATU (836 mg, 2.20 mmol, 1.5 equivalents) are added. The mixture is stirred at RT for three hours. Ethyl acetate is added, and the mixture is washed with saturated sodium bicarbonate solution. The aqueous phase is extracted once with ethyl acetate, and then the combined organic phases are washed with 1 M aqueous citric acid and again with saturated sodium bicarbonate solution, dried over sodium sulphate, filtered and concentrated in vacuo. The residue is chromatographed (method 16). Yield: 496 mg (74% of theory).

HPLC (method 9): $R_t$=3.94 min.

LC-MS (method 7): $R_t$=1.85 min; MS (ESIpos.): m/z (%)=456 (100) [M+H]$^+$.

$^1$H-NMR (300 MHz, d$_6$-DMSO): δ=0.80 (m, 9H), 1.10 (m, 3H), 1.30 (dd, 1H), 2.91 (dd, 1H), 3.12 (dd, 1H), 3.30 (s, 3H), 4.02 (m, 1H), 4.51 (m, 1H), 5.01 (d, 1H), 5.06 (d, 1H), 7.22 (dd, 1H), 7.30 (m, 5H), 7.63 (m, 1H), 8.40 (m, 2H).

Example 21A

N-[(Benzyloxy)carbonyl]-4,4-dimethyl-D-norleucyl-3-(pyridin-3-yl)-L-alanine

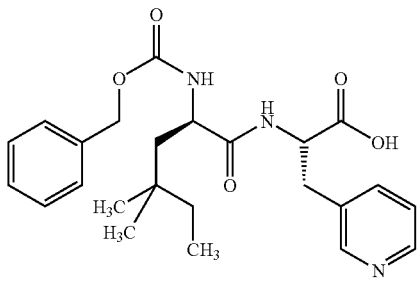

The compound from Example 20A (490 mg, 1.08 mmol) is dissolved in THF (5 ml). The solution is cooled to 0° C. and then 1.35 ml (2.7 mmol, 2.5 equivalents) of a 2 M solution of lithium hydroxide monohydrate in water are added and stirred vigorously for 1 h. Citric acid (1 M in water) is then added dropwise until the reaction is acidic, and the mixture is extracted with ethyl acetate. The organic extract is dried over sodium sulphate and concentrated. Yield: 484 mg (quant.).

HPLC (method 9): $R_t$=3.76 min.

LC-MS (method 7): $R_t$=1.88 min; MS (ESIpos.): m/z (%)=442 (100) [M+H]$^+$.

$^1$H-NMR (400 MHz, d$_6$-DMSO): δ=0.70 (m, 9H), 1.14 (m, 3H), 1.30 (dd, 1H), 2.64 (d, 1H), 2.75 (d, 1H), 2.89 (dd, 1H), 3.11 (dd, 1H), 4.03 (m, 1H), 4.45 (m, 1H), 4.98 (d, 1H), 5.05 (d, 1H), 7.22 (dd, 1H), 7.30 (m, 5H), 7.61 (m, 1H), 8.40 (m, 2H).

Example 22A

N-[(Benzyloxy)carbonyl]-4,4-dimethyl-D-norleucyl-3-(pyridin-3-yl)-L-alanyl-de(1-D-leucyl-2-L-leucyl)-lysobactin trifluoroacetate

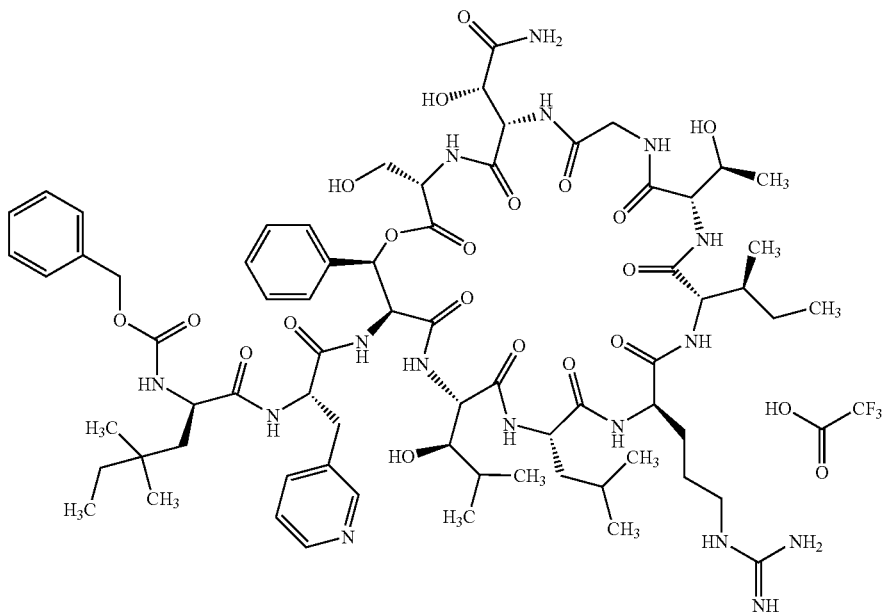

The compound from Example 2A (0.28 g, 0.22 mmol) and the compound from Example 21A (148 mg, 0.33 mmol, 1.5 equivalents) are dissolved in DMF (4 ml) and cooled to 0° C. Then firstly 110 0.47 ml (0.44 mmol, 2 equivalents) of a 1 M solution of N-methylmorpholine in DMF is added. Immediately thereafter HATU (141 mg, 0.37 mmol, 1.7 equivalents) is added and the mixture is stirred at 0° C. for 15 min. Then a further 0.44 ml (0.47 mmol, 2 equivalents) of the 1 M solution of 4-methylmorpholine in DMF is added dropwise. The mixture is then stirred at RT overnight. The mixture is purified on Sephadex LH 20 (method 3, mobile phase: methanol). The crude product is purified by preparative HPLC (method 13). Yield: 149 mg (43% of theory).

HPLC (method 9): $R_t$=3.93 min.

LC-MS (method 7): $R_t$=2.13 min, MS (ESIpos.): m/z (%)=737.4 (100) $[M+2H]^{2+}$, 1473 (2) $[M+H]^+$.

EXEMPLARY EMBODIMENTS

Example 1

3-tert-Butyl-D-alanyl-3-(6-trifluoromethylpyridin-3-yl)-L-alanyl-de(1-D-leucyl-2-L-leucyl)-lysobactin bistrifluoroacetate Trifluoroacetic acid (150 ml) is slowly added dropwise to a solution of the compound from Example 8A (10.3 g, 1.0 equivalent, 4.48 mmol, crude product) in dichloromethane (150 ml) at RT. The reaction mixture is stirred at RT (10 min), with complete conversion being observed by means of HPLC (method 9). The reaction mixture is concentration in a rotary evaporator and purified by preparative HPLC (method 11), resulting in 3.48 g (48% of theory) of product.

HPLC/UV-Vis (method 8): $R_t$=4.03 min.

HPLC/UV-Vis (method 9): $R_t$=3.64 min.

LC-MS (method 7): $R_t$=1.69 min; MS (ESIpos.): m/z (%)=697 (100) $[M+2H]^{2+}$, 1393 (5) $[M+H]^+$; MS (ESIneg.): m/z (%)=695 (100) $[M-2H]^{2-}$, 1391 (20) $[M-H]^-$ $^{19}$F-NMR (400 MHz, $d_5$-pyridine): δ=−67 (Ar—CF$_3$), −74 (CF$_3$COOH), −132 (1,4-dibromotetrafluorobenzene as reference). TFA content: 14.3% by weight.

HR-MS (method 1): $C_{62}H_{96}N_{16}O_{17}F_3$ $[M+H]^+$ calc. 1393.7091, found 1393.7119.

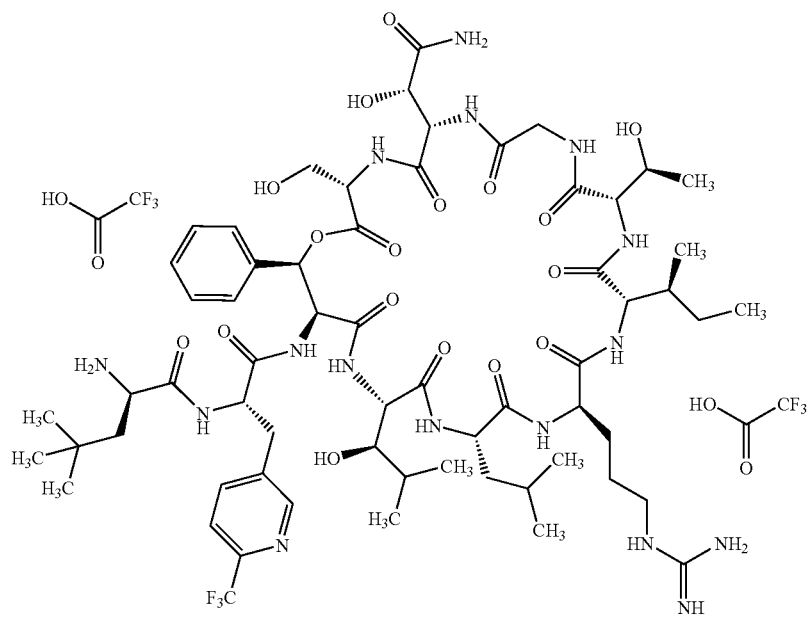

Example 2

3-(Trimethylsilyl)-D-alanyl-3-(pyridin-3-yl)-L-alanyl-de(1-D-leucyl-2-L-leucyl)-lysobactin tristrifluoroacetate

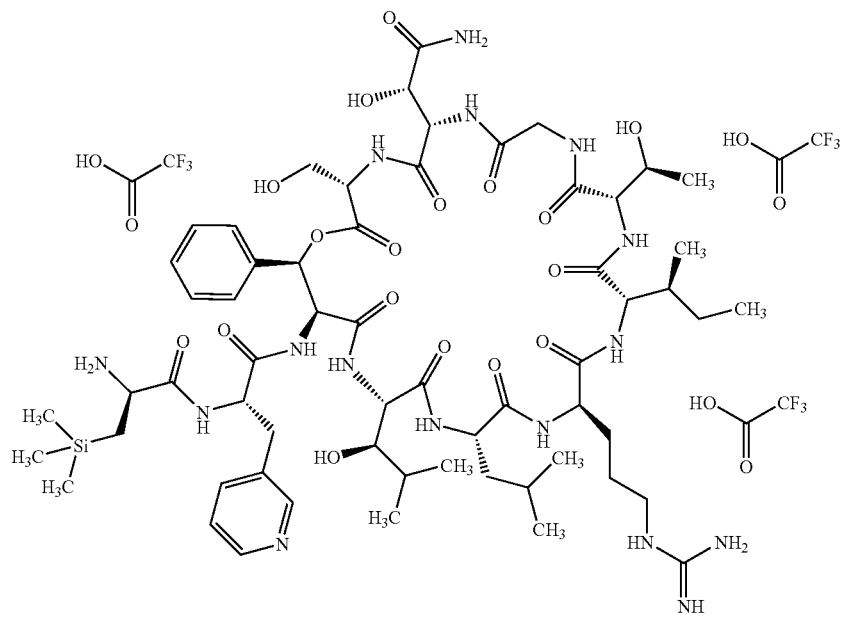

The compound from Example 15A (9.12 g, 4.93 mmol, crude product) is taken up in trifluoroacetic acid in dichloromethane (65 ml; 30% strength solution). The mixture is stirred at RT for 20 min. The solvent is distilled off. The residue is dried under oil pump vacuum and then purified by chromatography (method 14). Yield: 5.54 g (67% of theory).

HPLC (method 9): $R_t$=3.32 min.

LC-MS (method 7): $R_t$=1.41 min, MS (ESIpos.): m/z (%)=671.7 (100) [M+2H]$^{2+}$.

HR-TOF-MS (method 1): $C_{60}H_{97}N_{16}O_{17}Si$ [M+H]$^+$ calc. 1341.6987, found 1341.7019.

$^1$H-NMR (500 MHz, $d_5$-pyridine): δ=−0.172 (s, 9H), 0.611 (d, J=6.9 Hz, 3H), 0.881 (d, J=7.9 Hz, 3H), 0.948-(d, J=6.3 Hz, 3H), 0.954-0.997 (m, 6H), 1.135 (d, J=6.0 Hz, 3H), 1.208 (m, 2H), 1.361 (d, J=5.4 Hz, 3H), 1.439 (m, 1H), 1.497 (m, 1H), 1.953 (m, 2H), 2.04 (m, 1H), 2.154 (m, 3H), 2.372 (m, 3H), 3.111 (m, 1H), 3.266 (m, 1H), 3.563 (d, J=14.95 Hz, 1H), 3.726 (dd, J=12.2, 14.95 Hz, 1H), 3.840 (d, J=9.6 Hz, 1H), 3.960 (m, 1H), 4.152 (m, 1H), 4.198 (m, 1H), 4.278 (m, 1H), 4.382 (m, 1H), 4.488 (m, 1H), 4.565 (dd, J=9.5, 9.6 Hz, 1H), 4.628 (m, 1H), 4.630 (m, 1H), 4.779 (d, J=12.2 Hz, 1H), 5.069 (m, 1H), 5.159 (dd, J=9.3 Hz, 1H), 5.264 (m, 1H), 5.362 (s, 1H), 5.98 (d, J=9.9 Hz, 1H), 6.351 (dd, J=8.5 Hz, J=8.7 Hz, 1H), 7.169 (m, 1H), 7.246 (m, 1H), 7.382 (d, J=9.9 Hz, 1H), 7.512 (m, 2H), 7.583-7.614 (m, 2H), 7.728 (m, 2H), 7.90 (d, J=8.7 Hz, 1H), 8.126 (m, 3H), 8.341 (m, 1H), 8.576 (d, J=3.6 Hz, 1H), 8.695 (m, 2H), 8.793 (m, 1H), 9.139 (br s, 1H), 9.715 (m, 1H), 10.957 (br s, 1H), 11.268 (br s, 1H).

$^{13}$C-NMR (126 MHz, $d_5$-pyridine): δ=−1.8, 11.08, 15.84, 18.8, 18.8, 19.79, 20.89, 20.93, 21.65, 23.38, 24.78, 26.57, 26.88, 28.80, 31.04, 34.06, 36.84, 40.95, 41.25, 44.38, 50.94, 52.82, 55.99, 56.10, 56.74, 58.40, 59.10, 60.34, 60.72, 62.33, 62.55, 70.72, 72.06, 75.58, 75.65, 123.66, 128.25, 128.95, 129.80, 132.39, 136.77, 137.18, 149.17, 158.11, 162.15, 162.41, 162.70, 162.96, 169.01, 169.69, 170.21, 172.57, 173.27, 173.44, 173.66, 174.07, 174.36, 175.34, 175.56.

$^{19}$F-NMR (400 MHz, $d_5$-pyridine): δ=−74 ($CF_3COOH$), −132 (1,4-dibromotetrafluorbenzene as reference). TFA content: 19.3% by weight.

The structure is confirmed by a single-crystal X-ray structural analysis.

Example 3

3-(Trimethylsilyl)-D-alanyl-3-(pyridin-3-yl)-L-alanyl-de(1-D-leucyl-2-L-leucyl)-lysobactin trismethane-sulphonate

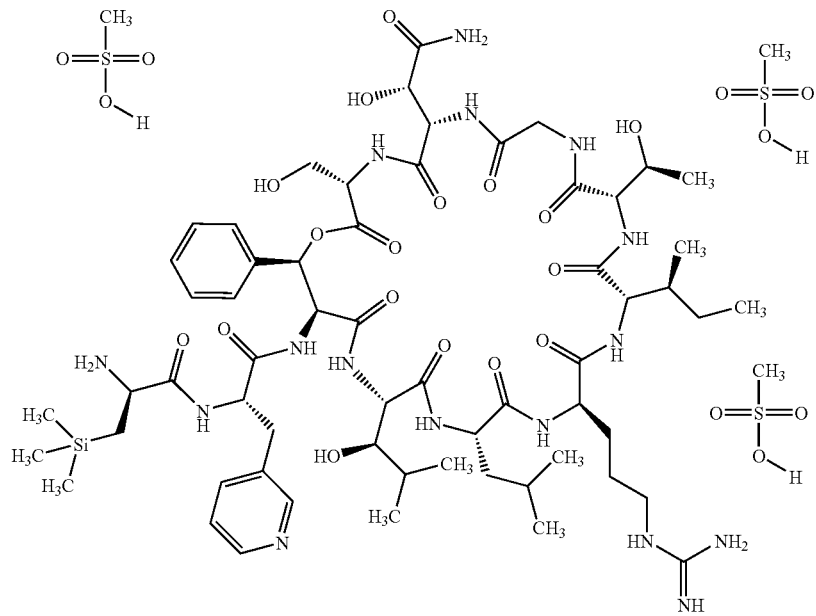

3-(Trimethylsilyl)-D-alanyl-3-(pyridin-3-yl)-L-alanyl-de(1-D-leucyl-2-L-leucyl)lysobactin tristrifluoroacetate (447 mg, 0.27 mmol) is dissolved in 22 ml of water. Methanesulphonic acid (70% strength) is added. The mixture is stirred vigorously and then lyophilized. The lyophilizate is taken up in water (3.4 ml), and 70% strength sodium methanesulphonate solution (0.9 ml) is added. The mixture is stirred at RT for 10 min. The product is then removed by centrifugation. 472 mg of crude product are obtained.

Crude products combined from several batches (total 1053 mg, 0.63 mmol) are suspended in water (5 ml) and stirred at RT for 4 days. Centrifugation is repeated, and the resulting solid is dried in vacuo. 575 mg (55% of theory) of the product are obtained.

HPLC (method 9): $R_t$=3.30 min.

LC-MS (method 7): $R_t$=1.49 min, MS (ESIpos.): m/z (%)=671.8 (100) [M+2H]$^{2+}$, 1342.1 (5) [M+H]$^+$.

$^1$H-NMR (500 MHz, d$_5$-pyridine): δ=−0.170 (s, 9H), 0.702 (d, J=6.3 Hz, 3H), 0.867 (d, J=6.1 Hz, 3H), 0.972 (d, J=6.2 Hz, 3H), 0.966-1.069 (m, 9H), 1.186 (d, J=6.5 Hz, 3H), 1.315 (m, 2H), 1.448-1.501 (m, 6H), 2.010 (m, 1H), 2.084 (m, 3H), 2.180-2.365 (m, 4H), 2.540 (m, 1H), 3.082 (s, 9H), 3.166 (m, 1H), 3.325 (m, 1H), 3.623 (d, J=14.05 Hz, 1H), 3.865 (dd, J=13.7, 14.05 Hz, 1H), 3.967-3.986 (m, 2H), 4.257 (m, 1H), 4.339 (m, 2H), 4.410 (m, 1H), 4.566 (m, 1H), 4.591-4.686 (m, 2H), 4.75 (d, 1H, J=12.1 Hz, 1H), 4.859 (m, 1H), 5.086 (m, 1H), 5.229 (m, 1H), 5.348 (m, 1H), 5.375 (s, 1H) 6.02 (d, J=10.0 Hz, 1H), 6.403 (m, 1H), 7.068 (d, J=9.8 Hz, 1H), 7.222 (m, 3H), 7.544 (m, 3H), 7.625 (m, 1H), 7.681 (m, 1H), 7.830 (d, J=7.6 Hz, 1H), 7.921 (d, J=9.35 Hz, 1H), 8.071 (m, 2H), 8.188 (br s, 1H), 8.285 (br s, 1H), 8.420 (d, J=8.4 Hz, 1H), 8.614 (d, J=4.0 Hz, 1H), 8.701 (m, 1H), 8.874 (br s, 1H), 10.175 (m, 1H), 10.279 (m, 1H), 10.941 (br s, 1H).

$^{19}$F-NMR (pyridine, 400 MHz, method 24): δ −74.0 (s, TFA, 0.20), −132.0 (s, 1,4-dibromotetrafluorobenzene, 1000.0), TFA=0.02% by weight.

Alternative process: 32 g of Dowex 1X8-400 (HCl form) are packed into a column (35 mm diameter). About 60 ml of 1 M sodium hydroxide solution are put onto the column, followed by 60 ml of HPLC water. This is followed by conditioning with 60 ml of 1 M methanesulphonic acid and subsequent washing with approximately 100 ml of water until the eluate has a neutral reaction. (Macherey & Nagel Tritest). Then 2.00 g (1.19 mmol) of 3-(trimethylsilyl)-D-alanyl-3-(pyridin-3-yl)-L-alanyl-de(1-D-leucyl-2-L-leucyl)lysobactin tristrifluoroacetate (Example 2) are dissolved in 90 ml of water, and the solution is loaded and slowly eluted. The column is washed with about 20 ml of water. Product-containing eluates are combined and subjected to microfiltration (pore size 0.20 μm) and lyophilization. The column is reconditioned and reused. 1.79 g (1.10 mmol, 92% of theory) of Example 3 are obtained from 2000 mg (1.19 mmol) of Example 2.

Example 4

4,4-Dimethyl-D-norleucyl-3-(pyridin-3-yl)-L-alanyl-de(1-D-leucyl-2-L-leucyl)lysobactin tristrifluoroacetate

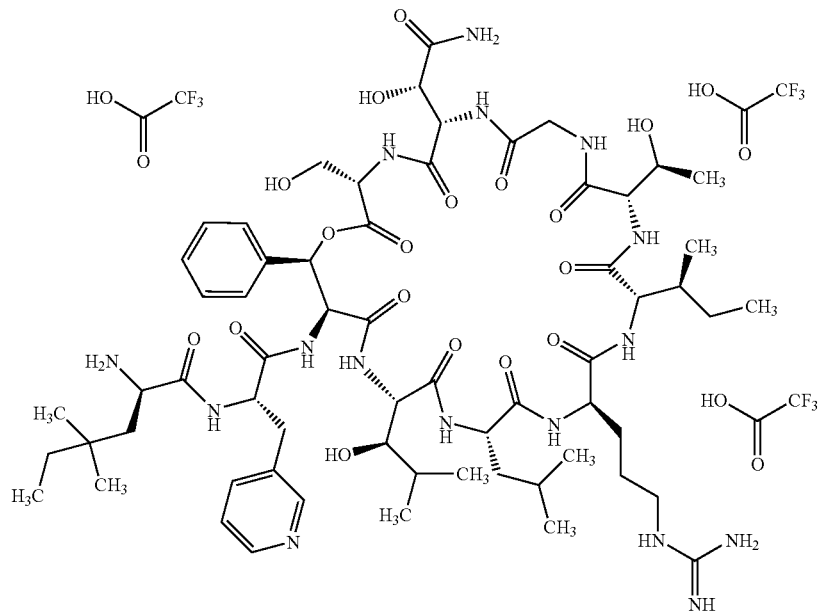

The compound from Example 22A (149 mg, 0.09 mmol) is dissolved in methanol/containing 0.05% trifluoroacetic acid (10 ml). Palladium on activated carbon (10%; 20 mg) is added and then hydrogenation is carried out under hydrogen at atmospheric pressure and at RT for 2.5 h in total. The crude product is filtered to remove the catalyst, and the filtrate is concentrated. The residue is purified by chromatography (method 13). Yield: 68 mg (46% of theory).

HPLC (method 9): $R_t$=3.29 min.

LC-MS (method 7): $R_t$=1.49 min, MS (ESIpos.): m/z (%)=671.0 (100) $[M+2H]^{2+}$, 1340 (5) $[M+H]^+$.

HR-TOF-MS (method 1): $C_{62}H_{98}N_{16}O_{17}$ $[M+H]^+$ calc. 1339.7369, found 1339.7368.

Example 5

Comparative Example 3-tert-Butyl-D-alanyl-3-(pyridin-3-yl)-L-alanyl-de(1-D-leucyl-2-L-leucyl)lysobactin tristrifluoroacetate

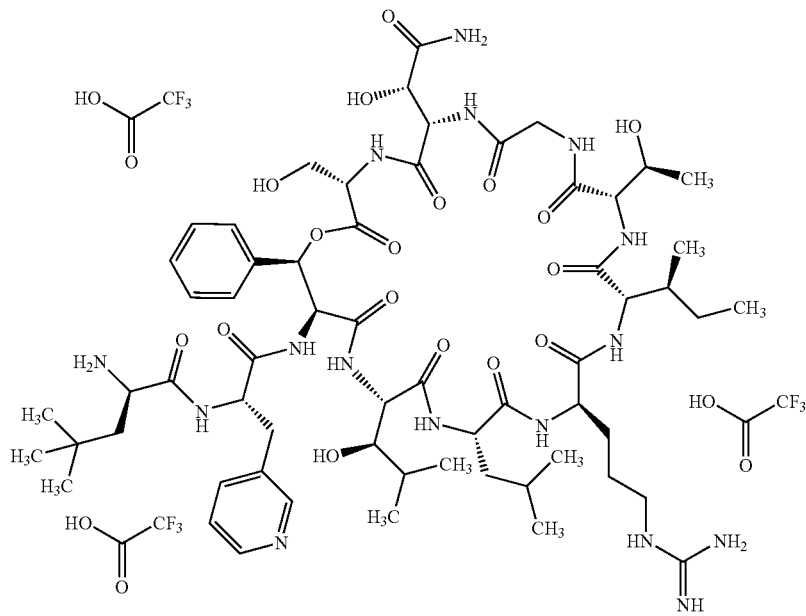

Example 6

(Trimethylsilyl)-D-alanyl-3-(pyridin-3-yl)-L-alanyl-de(1-D-leucyl-2-L-leucyl)lysobactin trishydrochloride

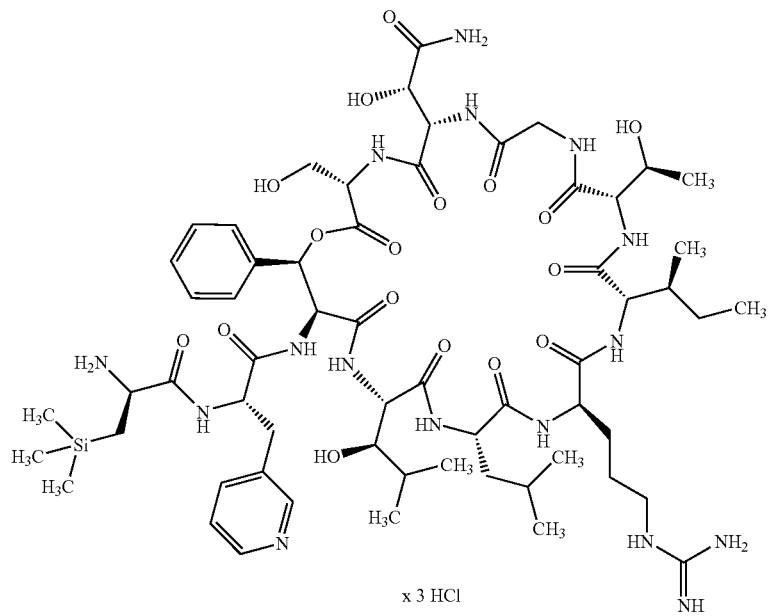

x 3 HCl 32 g of Dowex 1X8-400 (HCl form) are packed into a column (35 mm diameter). About 60 ml of 1 M sodium hydroxide solution are put onto the column, followed by 60 ml of HPLC water. This is followed by conditioning with 60 ml of 1 M hydrochloric acid and subsequent washing with approximately 100 ml of water until the eluate has a neutral reaction. (Macherey & Nagel Tritest). Then 2.00 g (1.19 mmol) of 3-(trimethylsilyl)-D-alanyl-3-(pyridin-3-yl)-L-alanyl-de(1-D-leucyl-2-L-leucyl)lysobactin tristrifluoroacetate (Example 2) are dissolved in 90 ml of water, and the solution is loaded and slowly eluted. The column is washed with about 20 ml of water. Product-containing eluates are combined and subjected to microfiltration (pore size 0.20 μm) and lyophilization. The column is reconditioned and reused. 1.54 g (1.06 mmol, 89% of theory) of Example 6 are obtained from 2000 mg (1.19 mmol) of Example 2.

HPLC (method 9): $R_t$=3.30 min.

LC-MS (method 7): $R_t$=1.47 min, MS (ESIpos.): m/z (%)=671.5 (100) $[M+2H]^{2+}$, 1341.4 (20), $[M+H]^+$.

Ion chromatography (method 25): Cl$^-$ (calc.)=7.43%, Cl$^-$ found=7.1%; TFA (found)<0.1%.

$^1$H-NMR (500 MHz, $d_5$-pyridine) δ=−0.170 (s, 9H), 0.580 (d, J=6.3 Hz, 3H), 0.772 (d, J=5.7 Hz, 3H), 0.920 (d, J=5.8 Hz, 3H), 0.974-0.985 (m, 6H), 1.147 (d, J=6.4 Hz, 3H), 1.250-1.358 (m, 2H), 1.411 (d, J=5.7 Hz, 3H), 1.468 (m, 1H), 1.604 (m, 1H), 1.959-2.049 (m, 3H), 2.154-2.228 (m, 3H), 2.380 (m, 3H), 2.935 (m, 1H), 3.120 (m, 1H), 3.300 (m, 1H), 3.607 (d, J=14.9 Hz, 1H), 3.762 (dd, J=14.7 Hz, 1H), 3.882 (d, J=9.1 Hz, 1H), 3.938 (m, 1H), 4.204 (m, 1H), 4.253 (m, 1H), 4.389 (m, 1H), 4.465 (m, 1H), 4.589-4.661 (m, 4H), 4.806 (d, J=12.1 Hz, 1H), 5.027 (m, 1H), 5.202 (dd, J=9.4 Hz, 1H), 5.289 (m, 1H), 5.390 (s, 1H), 6.000 (d, J=9.5 Hz, 1H), 6.394 (dd, J=9.0 Hz, 1H), 7.173 (m, 2H), 7.428 (m, 1H), 7.54 (d, J=7.0 Hz, 1H), 7.664-7.973 (m, 3H), 7.767 (d, J=8.6 Hz, 1H), 7.918-7.973 (m, 3H), 8.038 (br s, 2H), 8.098 (br s, 1H), 8.185 (br s, 1H), 8.253 (d, J=8.6 Hz, 1H), 8.582 (m, 1H), 8.684 (d, J=9.8 Hz, 1H), 8.741 (br s, 1H), 8.782 (m, 1H), 9.928 (br s, 1H), 10.272 (d, J=8.3 Hz, 1H), 10.886 (br s, 1H), 11.135 (br s, 1H).

$^{19}$F-NMR (pyridine, 400 MHz, method 24): TFA<limit of detection.

Example 7

(Trimethylsilyl)-D-alanyl-3-(pyridin-3-yl)-L-alanyl-de(1-D-leucyl-2-L-leucyl)lysobactin tris-L-lactate

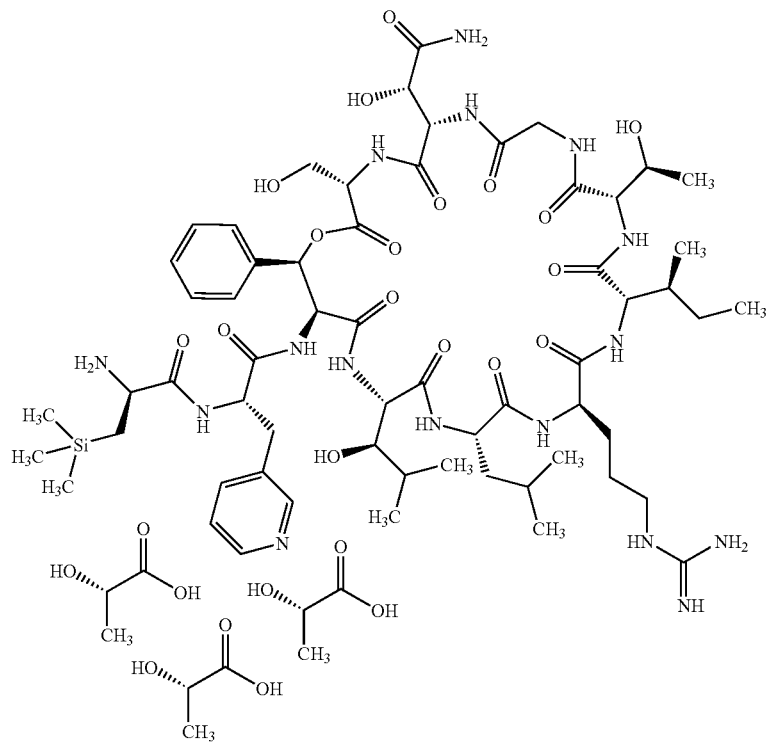

32 g of Dowex 1X8-400 (HCl form) are packed into a column (35 mm diameter). About 60 ml of 1 M sodium hydroxide solution are put onto the column, followed by 60 ml of HPLC water. This is followed by conditioning with 60 ml of 1 M lactic acid and subsequent washing with approximately 100 ml of water until the eluate has a neutral reaction. (Macherey & Nagel Tritest). Then 2.00 g (1.19 mmol) of 3-trimethylsilyl)-D-alanyl-3-pyridin-3-yl)-L-alanyl-de(1-D-leucyl-2-L-leucyl)lysobactin tristrifluoroacetate (Example 2) are dissolved in 90 ml of water, and the solution is loaded and slowly eluted. The column is washed with about 20 ml of water. Product-containing eluates are combined and subjected to microfiltration (pore size 0.20 μm) and lyophilization. The column is reconditioned and reused. 1903 mg (1.18 mmol, 99% of theory) of Example 7 are obtained from 2000 mg (1.19 mmol) of Example 2.

HPLC (method 9): $R_t$=3.29 min.

LC-MS (method 7): $R_t$=1.37 min, MS (ESIpos.): m/z (%)=671.7 (100) [M+2H]$^{2+}$, 1341.9 (20), [M+H]$^+$.

$^1$H-NMR (500 MHz, d$_5$-pyridine): δ=−0.170 (s, 9H), 0.754 (d, J=6.3 Hz, 3H), 0.836 (d, J=6.1 Hz, 3H), 0.922 (d, J=6.2 Hz, 3H), 0.922-0.957 (m, 6H), 1.054 (d, J=6.4 Hz, 3H), 1.190 (m, 2H), 1.416 (d, J=5.8 Hz, 3H), 1.439-1.662 (m, 4H), 1.529 (d, J=7.0 Hz, 3H), 1.598 (d, J=6.5 Hz, 3H), 1.669 (d, J=6.9 Hz, 3H), 1.923-2.280 (m, 9H), 3.057 (m, 1H), 3.266 (m, 1H), 3.564 (d, J=14.5 Hz, 1H), 3.761 (dd, J=13.7 Hz, 1H), 3.840 (m, 1H), 4.049 (m, 1H), 4.109 (m, 1H), 4.164 (m, 1H), 4.202 (m, 1H), 4.410 (m, 1H), 4.484 (m, 1H), 4.616 (dd, J=6.7, 13.6 Hz, 1H), 4.656 (m, 1H), 4.669 (dd, J=7.0, 13.9 Hz, 1H), 4.780 (d, J=13.0 Hz, 1H), 4.921 (m, 1H), 5.144 (dd, J=9.6 Hz, 1H), 5.281 (m, 1H), 5.363-5.426 (m, 3H) 5.362 (s, 1H), 5.989 (d, J=9.8 Hz, 1H), 6.323 (m, 1H), 7.122 (m, 1H), 7.180 (m, 1H), 7.381 (m, 1H), 7.596 (m, 1H), 7.671-7.925 (m, 6H), 8.036 (br s, 1H), 8.208 (m, 3H), 8.412 (m, 1H), 8.551 (d, J=3.6 Hz, 1H), 8.714 (m, 2H), 8.794 (m, 1H), 10.298 (br s, 1H), 10.938 (br s, 1H).

$^{19}$F-NMR (pyridine, 400 MHz, method 24): TFA<limit of detection.

Example 8

(Trimethylsilyl)-D-alanyl-3-(pyridin-3-yl)-L-alanyl-de(1-D-leucyl-2-L-leucyl)lysobactin tris-D-tartrate

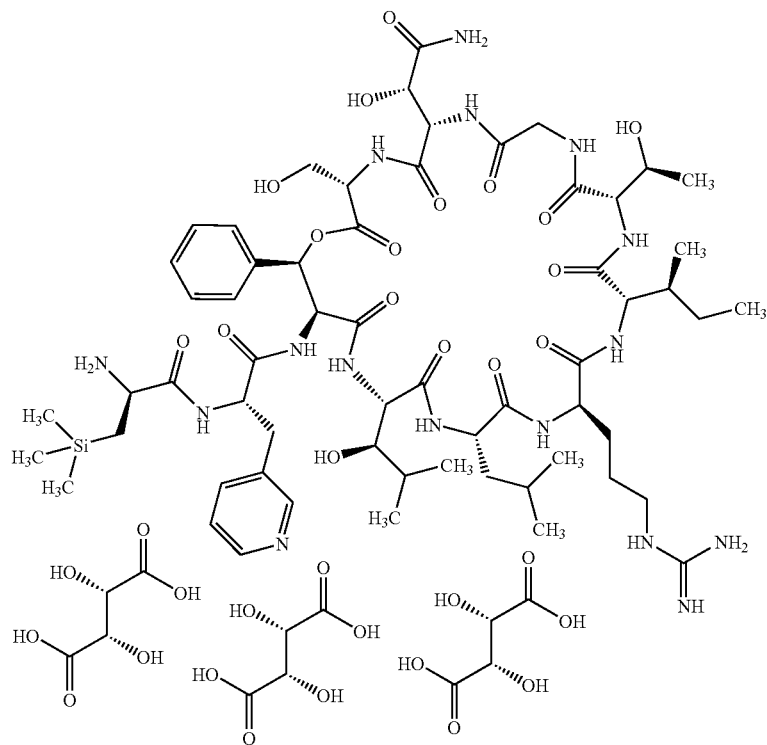

Conditioning of the ion exchanger: 5 g of DOWEX 1X8 400 (HCl salt) are washed with 1 M sodium hydroxide solution until the eluate has an alkaline reaction. This is followed by washing with 2 column volume of water and then with 1 M D-tartaric acid until the eluate has an acidic reaction. This is followed by washing with water until the eluate is neutral (Macherey & Nagel Tritest).

100 mg (59 μmol) of Example 2 are then dissolved in 10 ml of water and loaded onto the column. Washing is subsequently carried out with several portions of about 10 ml of water. The precursor dissolves only sparsely and part remains on the column. Product-containing eluate fractions are combined and lyophilized. 57 mg (31 μmol, 52% of theory) of the product are obtained. Integration of the $^1$H-NMR spectrum indicates a stoichiometry of 1:3 for (trimethylsilyl)-D-alanyl-3-(pyridin-3-yl)-L-alanyl-de(1-D-leucyl-2-L-leucyl)lysobactin:D-tartaric acid.

HPLC (method 9): $R_t$=3.29 min.

LC-MS (method 7): $R_t$=1.37 min, MS (ESIpos.): m/z(%)= 671.7 (100) [M+2H]$^{2+}$, 1341.9 (20), [M+H]$^+$.

$^1$H-NMR (500 MHz, d$_5$-pyridine): δ=−0.172 (s, 9H), 0.597 (d, J=6.3 Hz, 3H), 0.776 (d, J=5.7 Hz, 3H), 0.924 (d, J=5.8 Hz, 3H), 0.954-0.997 (m, 6H), 1.173 (d, J=5.7 Hz, 3H), 1.303 (m, 2H), 1.434 (d, J=5.7 Hz, 3H), 1.468 (m, 1H), 1.632 (m, 1H), 1.972 (m, 2H), 2.051 (1H, m), 2.174 (m, 3H), 2.402 (m, 3H), 3.129 (m, 1H), 3.305 (m, 1H), 3.602 (d, J=15.2 Hz, 1H), 3.799 (dd, J=14.6 Hz, 1H), 3.893 (d, J=12.3 Hz, 1H), 3.967 (m, 1H), 4.228 (m, 1H), 4.276 (m, 1H), 4.409 (m, 1H), 4.468 (m, 1H), 4.578-4.669 (m, 4H), 4.791 (d, J=11.5 Hz, 1H), 5.044 (m, 1H), 5.226 (dd, J=9.4 Hz, 1H), 5.190 (m, 1H), 5.362 (s, 1H), 5.417 (s, 6H), 5.997 (d, J=9.7 Hz, 1H), 6.403 (dd, J=8.9 Hz, 1H), 7.182 (m, 1H), 7.551-8.210 (m, 13H), 8.589 (d, J=3.6 Hz, 1H), 8.711 (d, J=10.0 Hz, 1H), 8.782 (m, 2H), 9.902 (br s, 1H), 10.358 (m, 1H), 10.882 (br s, 1H), 11.093 (br s, 1H).

Example 9

(Trimethylsilyl)-D-alanyl-3-(pyridin-3-yl)-L-alanyl-de(1-D-leucyl-2-L-leucyl)lysobactin

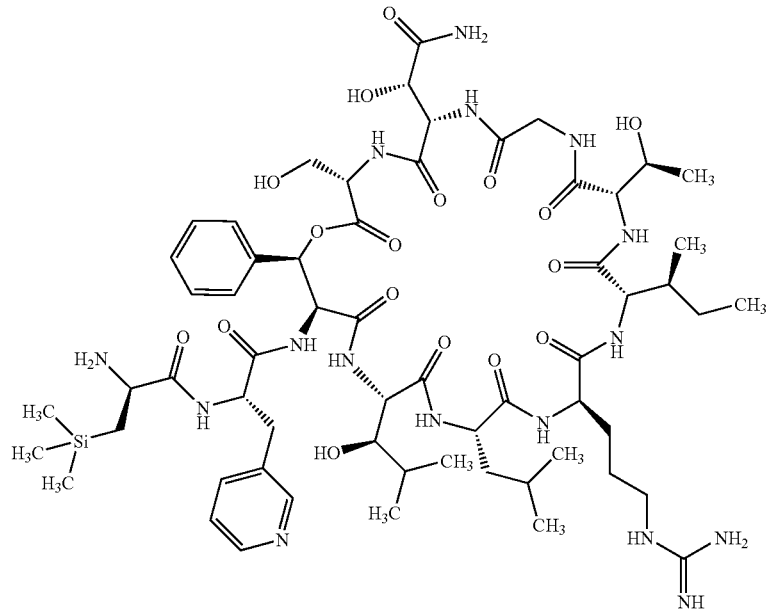

Polymer-bound bicarbonate PL-HCO$_3$ (Polymer Labs, capacity 1.8 mmol/g) is packed into a column. 396 mg (corresponds to 12 equivalents of bicarbonate) of the resin are used to react 100 mg (59 µmol) of the compound of Example 2. The resin is washed with pyridine. Then a solution of Example 2 (100 mg, 59 µmol) in pyridine (0.75 ml) is put onto the column and slowly eluted. The column is washed firstly with further pyridine (2 ml) and then with water (about 2 ml). All the eluates are combined and concentrated under oil pump vacuum without heat input. The glassy residue is dissolved in a few drops of water and freeze dried without delay. The title compound is obtained as a colourless amorphous powder.

HPLC (method 9): $R_t$=3.30 min.

LC-MS (method 7): $R_t$=1.49 min, MS (ESIpos.): m/z (%)=671.8 (100) [M+2H]$^{2+}$, 1341.9 (10), [M+H]$^+$, MS (ESIneg): m/z (%)=669.9 (100) [M−2H]$^{2-}$, 1340.0 (100) M−H]$^-$.

$^{19}$F-NMR (pyridine, 400 MHz, method 24): TFA 2.9%.

Example 10

(Trimethylsilyl)-D-alanyl-3-(pyridin-3-yl)-L-alanyl-de(1-D-leucyl-2-L-leucyl)lysobactin mesylate trifluoroacetate

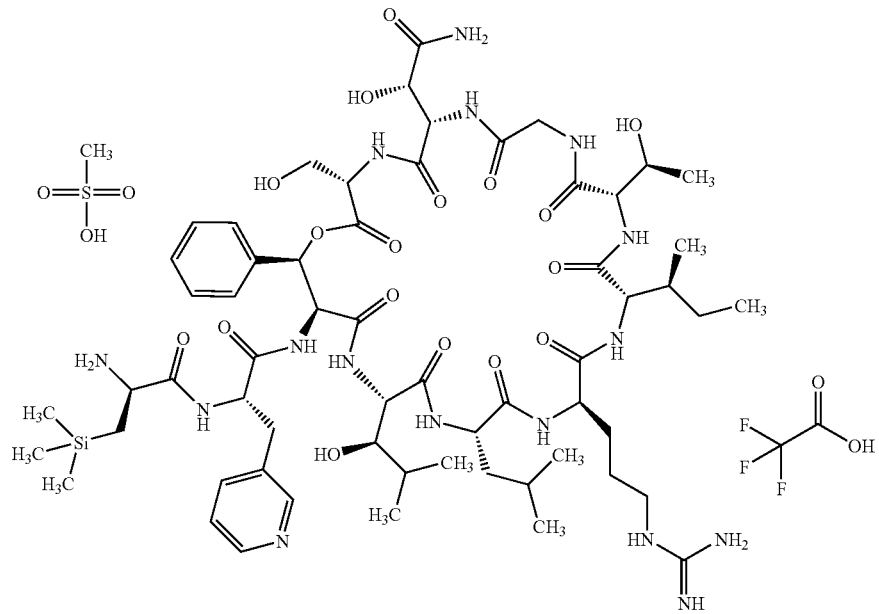

The title compound can be obtained as crystalline substance by recrystallization of Example 3 from TFA-doped water at RT (slow evaporation of the solution).

LC-MS (method 6): $R_t$=1.41 min, MS (ESIpos.): m/z (%)=671.9 (100) $[M+2H]^{2+}$, 1342.1 (10), $[M+H]^+$, MS (ESIneg): m/z (%)=669.9 (100) $[M-2H]^{2-}$, 1340.1 (80) $M-H]^-$.

HR-TOF-MS (method 1): $C_{60}H_{97}N_{16}O_{17}Si$ $[M+H]^+$ calc. 1341.6982, found 1341.7006.

The structure and the salt form is confirmed by a single-crystal X-ray structural analysis.

B. ASSESSMENT OF THE PHYSIOLOGICAL ACTIVITY

The in vitro effect of the compounds of the invention can be shown in the following assays:

Determination of the Minimum Inhibitory Concentration (MIC):

The MIC is determined in the liquid dilution test in accordance with the NCCLS guidelines. Overnight cultures of *Staphylococcus aureus* 133, *Enterococcus faecalis* 27159, *E. faecium* 4147 and *Streptococcus pneumoniae* G9a are incubated with the described test substances in a 1:2 dilution series. The MIC determination is carried out with a cell count of $10^5$ microbes per ml in Isosensitest medium (Difco, Irvine/USA), with the exception of *S. pneumoniae* which is tested in BHI broth (Difco, Irvine/USA) with 10% bovine serum with a cell count of $10^6$ microbes per ml. The cultures are incubated at 37° C. for 18-24 hours, *S. pneumoniae* in the presence of 10% $CO_2$.

The MIC is defined as the lowest concentration of each substance at which visible bacterial growth no longer occurs. The MIC values are reported in µg/ml.

Representative in-vitro effect data and $f_u$ data for the compounds of the invention are shown in Table A:

TABLE A

| Example No. | MIC S. aureus 133 [µg/ml] | MIC S. pneumoniae G9a [µg/ml] | MIC E. faecium L4001 [µg/ml] | MIC E. faecalis ICB 27159 [µg/ml] | $f_u$ (rat) [%] |
|---|---|---|---|---|---|
| 2 | 0.125 | 0.125 | 1 | 0.5 | 12.3 |
| 3 | 0.5 | 0.125 | 1 | 0.5 | — |
| 4 | 0.25 | 0.125 | — | 1 | 6.1 |
| 5 | 0.5 | 0.5 | 1 | 1 | 8.6 |
| 6 | <0.063 | <0.063 | — | 1 | — |
| 7 | 0.063 | 0.125 | — | 1 | — |
| 8 | 0.25 | 0.125 | — | 2 | — |
| 1A | 0.5 | 0.063 | 0.5 | 0.5 | 0.67 |

The suitability of the compounds of the invention for the treatment of bacterial infections can be shown in the following animal model:

Systemic Infection with *Staphylococcus aureus* 133:

Cells of *S. aureus* 133 are grown overnight in BHI broth (Oxoid, N.Y./USA). The overnight culture is diluted 1:100 in fresh BIB broth and incubated for 3 hours. The cells which are then in the logarithmic phase of growth are spun down and washed twice with buffered physiological saline. Then a cell suspension in saline is adjusted photometrically to an extinction of 50 units. After a dilution step (1:15), the suspension is mixed 1:1 with a 10% strength mucin solution. 0.25 ml of this infection solution are administered intraperitoneally per 20 g mouse (equivalent to $1 \times 10^6$ microbes/mouse). Therapy takes place intraperitoneally or intravenously 30 minutes after the infection. Female CFW1 mice are used for the infection test. The survival of the animals is recorded over 6 days.

The properties of the compounds of the invention in relation to renal tolerability can be shown in the following animal model:

Mouse Model for Determining Nephrotoxic Effects:

Nephrotoxic side effects of the nonadepsipeptides are analysed by histopathological examinations of the kidneys in mice after multiple administration of a particular dosage. For this purpose, 5-6 animals are treated each day either intravenously (i.v.) or intraperitoneally (i.p.) with substances which are dissolved in aqueous solution or with addition of Solutol. Nephrotoxic effects are determined by optical microscopic assessment of haematoxylin and eosin (H&E) stained paraffin sections of the kidneys. A periodic acid shift (PAS) reaction is optionally carried out to visualize glycoproteins better. Nephrotoxic effects are specified semiquantitatively for each animal as severities of the tubular basophilia and degeneration/regeneration occurring (severities: 0=no effect; 1=minimal effect; 2=slight effect; 3=moderate effect; 4=severe lesions). The average severity of the tubular degeneration/regeneration and the incidence (number of affected aminals) is calculated for each animal group or derivative. Renal changes going beyond this, such as tubular dilatation and necroses and accumulation of necrotic material, are likewise listed.

Rat Model for Determining Nephrotoxic Effects:

Nephrotoxic side effects of the nonadepsipeptides are analysed by histopathological examinations of the kidney in rats after multiple administration of a particular dosage. For this purpose, 5 animals are treated each day intravenously (i.v.) with substances which are dissolved in saline or Ringer's lactate solution. Nephrotoxic effects are determined by optical microscopic assessment of haematoxylin and eosin (H&E) stained paraffin sections of the kidneys. A periodic acid shift (PAS) reaction is optionally carried out to visualize glycoproteins better. Nephrotoxic effects are specified semiquantitatively for each animal as severities of the tubular basophilia and degeneration/regeneration occurring (severities: 0=no effect; 1=minimal effect; 2=slight effect; 3=moderate effect; 4=severe lesions). The average severity of the tubular degeneration/regeneration and the incidence (number of affected animals) is calculated for each animal group or derivative. Renal changes going beyond this, such as tubular dilatation and necroses and accumulation of necrotic material, are likewise listed.

Principle of the Determination of the Free Fraction via Transil:

The method described herein for determining the free fraction ($f_u$) of a test substance is divided into 2 parts:

a) Determination of the Transil®/buffer partitioning ratio ($MA_{buffer}$) by incubating the test substance in a Transil® buffer (pH 7.4) dispersion and subsequently determining the concentration in the dispersion and in the buffer supernatant.

b) Determination of the Transil®/plasma partitioning ratio ($MA_{plasma}$) by incubating the test substance in a Transil® plasma dispersion and subsequently determining the concentration in the dispersion and in the plasma.

The quotient of the two partitioning ratios gives $f_u$.

Where substances are highly protein-bound, the plasma is usually diluted with isotonic phosphate buffer (pH 7.4) and then suspended with Transil®. Determination of $f_u'$ (free fraction in diluted plasma) in this diluted protein solution takes place in analogy to the determination of $f_u$. The free fraction in undiluted plasma is calculated from $f_u'$ and the dilution factor.

Concerning this method, compare also: Schuhmacher, Joachim; Kohlsdorfer, Christian; Buehner, Klaus; Brandenburger, Tim; Kruk, Renate, "High-throughput determination of the free fraction of drugs strongly bound to plasma proteins." *Journal of Pharmaceutical Sciences* 2004, 93, 816-830.

Determination of the Membrane Affinity of a Test Substance After Partitioning Between Transil® and Buffer ($MA_{buffer}$):

All incubations are carried out in suitable glass vessels, e.g. glass vials, ground-joint test tubes. The total volume is usually 0.5-5 ml, and the Transil® volume is 10-100 μl. If the membrane affinities are expected to be high, the Transil® dispersion can be diluted up to 20 times with phosphate buffer of pH 7.4, e.g. Dulbecco's PBS. Phosphate buffer of pH 7.4 is introduced into the incubation vessels, and the Transil® is pipetted in after thorough mixing. The test substance is pipetted in at a concentration of, for example, 200 ng/ml, n=6. The proportion of organic solvents should be ≦2%. The mixtures are incubated at room temperature i.e. on a mini-shaker at an angle of about 45°, at about 400 rpm for 30 min. The 100% value is determined by taking at least one aliquot of, for example, 100 μl, and the remaining mixture is centrifuged at about 1800 g for about 10 min. At least 2 aliquots (e.g. 100 μl) of the supernatant are taken from each sample for the concentration determination.

Determination of $MA_{plasma}$ in Undiluted or Diluted Plasma:

The total incubation volume and the added volume of Transil® depend on the expected free fraction. The total volume is usually 0.5-1 ml, and the Transil® volume is 10-100 μl. If the free fractions are very low, the plasma of the species to be investigated is diluted e.g. 10-400 times with isotonic buffer solution, pH 7.4, and then Transil® is added. The subsequent procedure is as described above for determining the $MA_{buffer}$ values.

Principle of the Determination of the Free Fraction via Ultrafiltration:

The plasma of the species to be investigated is filtered through a semipermeable membrane. The concentration of substance in the filtrate is measured, and the free fraction $f_u$ is calculated therefrom. The Centrifree micropartition system from Millipore/Amicon is used. The ultrafiltration membranes have an exclusion size of 30 000 Da. 1 ml of plasma is doped with the substance in a concentration of about 1 μg/ml. The proportion of solvent should be <2%. After incubation at room temperature for 30 minutes, the plasma is pipetted into the ulftrafiltration system and centifuged at 1800 g for 10 minutes. The concentration of substance in the ultrafiltrate ($C_u$, unbound substance concentration) and in the plasma before centrifugation (C; total substance concentration) is measured. The free fraction is calculated by the formula $f_u$ (%)=$C_u$/C*100.

C. EXEMPLARY EMBODIMENTS OF PHARMACEUTICAL COMPOSITIONS

The compounds of the invention can be converted into pharmaceutical preparations in the following ways:

Tablet:

Composition:
100 mg of the compound of Example 1, 50 mg of lactose (monohydrate), 50 mg of maize starch (native), 10 mg of polyvinylpyrolidone (PVP 25) (BASF, Ludwigshafen, Germany) and 2 mg of magnesium stearate.

Tablet weight 212 mg. Diameter 8 mm, radius of curvature 12 mm.

Production:
A mixture of active ingredient, lactose and starch is granulated with a 5% strength solution (m/m) of PVP in water. The granules are dried and then mixed with the magnesium stearate for 5 min. This mixture is compressed with a conventional tablet press (see above for format of the tablet). A compressive force of 15 kN is used as guideline for the compression.

Suspension Which Can be Administered Orally:

Composition:
1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.

Production:
The Rhodigel is suspended in ethanol, and the active ingredient is added to the suspension. The water is added while stirring. The mixture is stirred for about 6 h until the swelling of the Rhodigel is complete.

Solution Which Can Administered Intravenously:

Composition:
100-200 mg of the compound of Example 1, 15 g of polyethylene glycol 400 and 250 g of water for injection.

Production:
The compound of Example 1 is dissolved together with polyethylene glycol 400 in the water with stirring. The solution is sterilized by filtration (pore diameter 0.22 μm) and used to fill heat-sterilized infusion bottles under aseptic conditions. The latter are closed with infusion stoppers and crimped caps.

The invention claimed is:
1. A compound of the formula

(I)

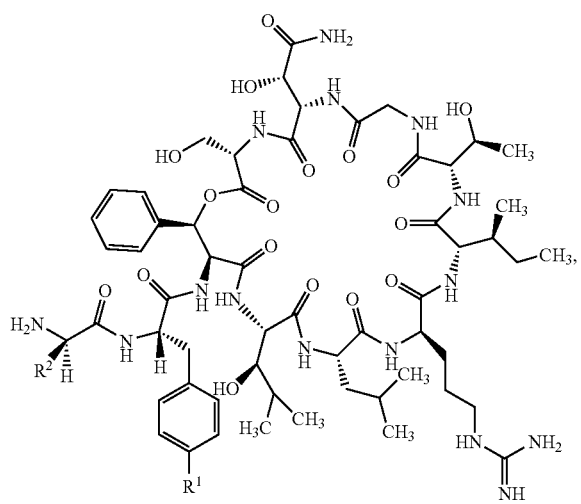

in which
R¹ is hydrogen, and
R² is 2-ethyl-2-methylbut-1-yl, 2,2-diethylbut-1-yl, 2,2-dimethylpent- 1-yl or trimethylsilylmethyl,
or
R¹ is trifluoromethyl, and
R² is 2,2-dimethyipropp- 1-yl, 2,2-dimethylbut- 1-yl, 2-ethyl-2-methylbut- 1-yl, 2,2-diethylbut- 1-yl, 2,2-dimethylpent- 1-yl or trimethylsilylmethyl,
or one of its salts.

2. The compound according to claim 1, wherein
R¹ is hydrogen, and
R² is trimethylsilylmethyl,
or
R¹ is trifluoromethyl, and
R² is 2,2-dimethylprop-1 -yl, 2,2-dimethylbut-1 -yl or trimethylsilylmethyl.

3. The compound according to claim 1, wherein
R¹ is hydrogen, and
R² is 2-ethyl-2-methylbut-1 -yl, 2,2-diethylbut-1 -yl or trimethylsilylmethyl.

4. The compound according to claim 1 having the following structure 3-(trimethylsilyl)-D-alanyl-3-(pyridin-3 -yl)-L-alanyl-de( 1 -D-leucyl-2-L-leucyl)lysobactin

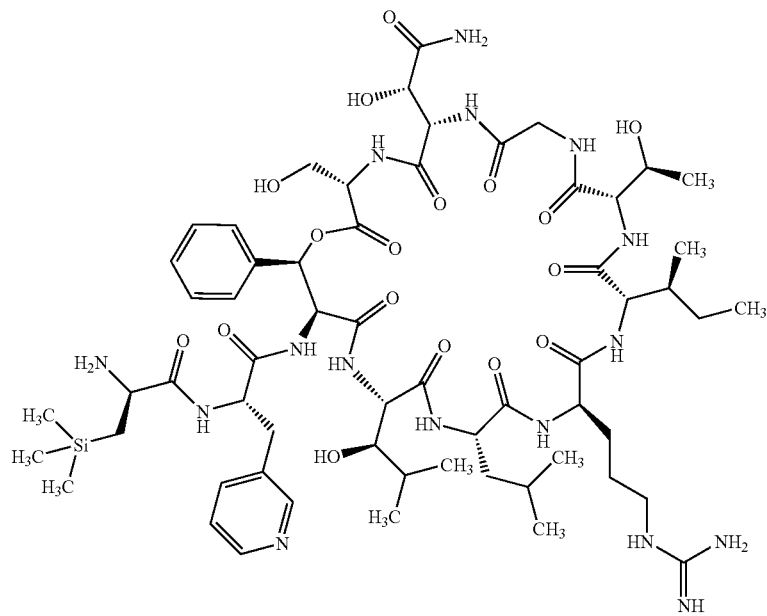

or one of its salts.

5. A process for preparing a compound of the formula (I) according to claim 1, comprising reacting the compound of the formula

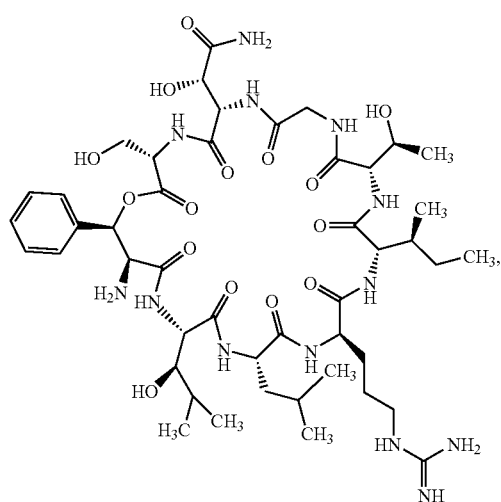

(II)

with a compound of the formula

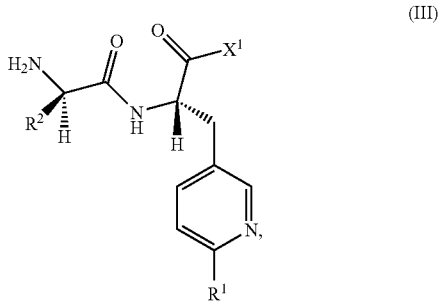

(III)

in which $R^1$ and $R^2$ have the meaning indicated in claim 1, and $X^1$ is halogen or hydroxy.

6. A medicament comprising a compound according to any of claims 1 to 4 in combination with an inert, non-toxic, pharmaceutically suitable excipient.

7. The medicament according to claim 6 for the treatment of bacterial infections.

8. A method for controlling bacterial infections in humans and animals in need thereof by administration of an antibacterially effective amount of at least one compound according to any of claims 1 to 4.

9. A method for controlling bacterial infections in humans and animals in need thereof by administration of an antibacterially effective amount of a medicament according to claim 6.

* * * * *